US012736546B2

(12) United States Patent
Rai et al.

(10) Patent No.: US 12,736,546 B2
(45) Date of Patent: Sep. 15, 2026

(54) METHODS, SYSTEMS, AND A KIT FOR DIAGNOSIS, DETECTION, MONITORING AND TREATMENT OF TRAUMATIC BRAIN INJURY

(71) Applicant: RapidDx Inc., New Berlin, WI (US)

(72) Inventors: Balwant Rai, Dragor (DK); Jasdeep Kaur, Dragor (DK)

(73) Assignee: RapidDx, Inc., New Berlin, WI (US)

( * ) Notice: Subject to any disclaimer, the term of this patent is extended or adjusted under 35 U.S.C. 154(b) by 1314 days.

(21) Appl. No.: 17/296,499

(22) PCT Filed: Nov. 25, 2019

(86) PCT No.: PCT/IN2019/050864
§ 371 (c)(1),
(2) Date: May 24, 2021

(87) PCT Pub. No.: WO2020/110143
PCT Pub. Date: Jun. 4, 2020

(65) Prior Publication Data

US 2023/0135030 A1 May 4, 2023

(30) Foreign Application Priority Data

Nov. 26, 2018 (IN) ............................. 201811044520

(51) Int. Cl.
*G01N 33/68* (2006.01)
*G01N 33/534* (2006.01)

(52) U.S. Cl.
CPC ....... *G01N 33/6896* (2013.01); *G01N 33/534* (2013.01); *G01N 2800/2871* (2013.01)

(58) Field of Classification Search
CPC ............. G01N 33/6896; G01N 33/534; G01N 2800/2871
See application file for complete search history.

(56) References Cited

U.S. PATENT DOCUMENTS 6,911,198 B2 6/2005 Shachar et al.
6,974,809 B2 12/2005 Golec et al.
8,871,155 B2 10/2014 Wu et al.
9,198,641 B2 12/2015 Slowey et al.
9,529,002 B2 12/2016 Rai et al.
9,927,445 B2 3/2018 Rai et al.
10,023,903 B2 7/2018 Wong et al.
10,041,959 B2 8/2018 Wang et al.
10,739,335 B2 8/2020 Harel
11,016,105 B2 5/2021 McQuiston et al.
2009/0208508 A1 8/2009 Lee et al.
2012/0295281 A1 11/2012 Rai et al.
2012/0322682 A1 12/2012 McDevitt et al.
2013/0121962 A1 5/2013 Francis et al.
2014/0024053 A1* 1/2014 Kobeissy ........... G01N 33/6896 435/7.1
2014/0072982 A1 3/2014 Rai et al.
2014/0303041 A1* 10/2014 Hayes .................... C07K 16/18 506/18
2014/0322734 A1 10/2014 Rai et al.
2015/0239951 A1 8/2015 Szymkowski et al.
2016/0011183 A1 1/2016 Egan et al.
2017/0067913 A1 3/2017 Rai et al.
2018/0003723 A1 1/2018 Rai et al.
2018/0031383 A1 2/2018 Chang et al.
2018/0038852 A1 2/2018 Manuguerra et al.
2018/0106799 A1 4/2018 Brenner et al.
2018/0143187 A1 5/2018 Henkin
2018/0235206 A1 8/2018 Laughlin et al.
2018/0284139 A1 10/2018 Rai et al.
2019/0053744 A1 2/2019 Janigro et al.
2019/0128813 A1 5/2019 Clarke et al.
2020/0003772 A1 1/2020 Harel et al.
2020/0013488 A1 1/2020 Lui et al.
2022/0050111 A1 2/2022 Datwyler et al.

FOREIGN PATENT DOCUMENTS

EP 2836844 10/2013
IN 201711027532 3/2019
MX 358474 8/2018
WO 2013153461 10/2013
WO 2020110143 6/2020
WO 2020110143 A1 6/2020
WO 2021198884 10/2021

OTHER PUBLICATIONS

Kulbe and Geddes, Experimental Neurology, 275: 334-352, (Year: 2016).*
Papa et al., J Trauma Acute Care Surg, 72(5): 1335-1344, May (Year: 2012).*
[Abstract Only {full reference has been ordered}] Role of Salivary Biomarkers in Predicting Significant Traumatic Brain Injury, Yeung et al., Pediatrics, 141 (1_MeetingAbstract): 357, published on Jan. 1, (Year: 2018).*
Zetterberg, Henrik, et al., Fluid Biomarkers for Mild Traumatic Brain Injury and Related Conditions, Nature Reviews Neurology, vol. 12, No. 10, pp. 563-574, (2016) (DOI: 10.1038/nrneurol.2016.127).

(Continued)

*Primary Examiner* — Stacey N Macfarlane
(74) *Attorney, Agent, or Firm* — Jansson Munger & McKinley Ltd.

(57) ABSTRACT

Methods and systems for diagnosis, detection, monitoring, and treatment of traumatic brain injury are described. The methods and systems include detection of salivary biomarkers associated with brain injury in a human subject, one application of which is to determine whether the subject has sustained a concussion or a more severe traumatic brain injury (TBI). Detection of the salivary biomarkers can also provide a basis to determine that a subject can safely return to play in an athletic event and can provide a basis to evaluate the efficacy of particular treatments. The methods and systems may be implemented, for example, by means of a kit.

35 Claims, No Drawings

(56) References Cited

OTHER PUBLICATIONS

Loo, J.A., et al., Comparative Human Salivary and Plasma Proteomes, J Dent Res 89(10): 1016-1023 (2010) (DOI: 10.1177/0022034510380414).
Schmechel D., et al., Neurone-Specific Enolase is a Molecular Marker for Peripheral and Central Neuroendocrine Cells, Nature, 276:834-836 (1978) (DOI: 10.1038/276834a0).
Dash, Pramod, et al, Biomarkers for the Diagnosis, Prognosis, and Evaluation of Treatment Efficacy for Traumatic Brain Injury, Neurotherapeutics, 7(1):100-14 (2010) (DOI: 10.1016/j.nurt.2009.10.019).
Skogseid, I. M., et al., Increased Serum Creatine Kinase BB and Neuron Specific Enolase Following Head Injury Indicates Brain Damage, Acta Neurochir (Wien.), 115(3-4): 106-11 (1992) (DOI: 10.1007/BF01406367).
Gill, Jessica, et al., Glial Fibrillary Acidic Protein Elevations Relate to Neuroimaging Abnormalities after Mild TBI, Neurology, 91(15) (2018) (DOI: 10.1212/WNL.0000000000006321).
Gardner, Raquel, et al., Age-Related Differences in Diagnostic Accuracy of Plasma Glial Fibrillary Acidic Protein and Tau for Identifying Acute Intracranial Trauma on Computed Tomography: A Track—TBI Study, J. Neurotrauma, 35(20):2341-2350 (2018) (DOI: 10.1089/neu.2018.5694).
Rhine, Tara, et al., Are UCH-LI and GFAP Promising Biomarkers for Children with Mild Traumatic Brain Injury? Brain Inj. 30(10):1231-8 (2016) (DOI: 10.1080/02699052.2016.1178396).
Mondello, S., et al., Clinical Utility of Serum Levels of Ubiquitin C-Terminal Hydrolase as a Biomarker for Severe Traumatic Brain Injury, Neurosurgery, 70(3): 666-675 (2012) (DOI:10.1227/NEU.0b013e318236a809).
Ost, M., et al., Initial CSF Total Tau Correlates with 1-year Outcome in Patients with Traumatic Brain Injury, Neurology, 67 (9):1600-1604 (2006) (DOI:10.1212/01.wnl.0000242732.06714.0f).
Liu, M.C., et al., Ubiquitin Cterminal Hydrolase-LI as a Biomarker for Ischemic and Traumatic Brain Injury in Rats, Eur J. Neurosci, 31(4):722-732 (2010) (DOI: 10.1111/j.1460-9568.2010.07097.x.).
Quagliarello, V.J., et al., Recombinant Human Interleukin-1 Induces Meningitis and Blood-Brain Barrier Injury in the Rat. Characterization and Comparison with Tumor Necrosis Factor, J. Clin. Invest., 87(4):1360-6. (1991).
Frugier, Tony, et al., In Situ Detection of Inflammatory Mediators in Post-Mortem Human Brain Tissue After Traumatic Injury, J. Neurotrauma, 27(3): 497-507 (2010) (DOI: 10.1089/neu.2009.1120).
Singhal, A., et al., Association Between Cerebrospinal Fluid Interleukin-6 Concentrations and Outcome after Severe Human Traumatic Brain Injury, J. Neurotrauma, 19(8):929-937 (2002) (DOI: 10.1089/089771502320317087).
Buttram, S.D., et al., Multiplex Assessment of Cytokine and Chemokine Levels in Cerebrospinal Fluid Following Severe Pediatric Traumatic Brain Injury: Effects of Moderate Hypothermia, J. Neurotrauma, 24(11): 1707-1718 (2007) (DOI: 10.1089/neu.2007.0349).
Tasci, A., et al., Prognostic Value of Interleukin-1 Beta Levels After Acute Brain Injury. Neural. Res. 25(8): 871-874 (2003) (DOI: 10.1179/016164103771953998).
Chiaretti, A., et al., Interleukin 1β and Interleukin 6 Relationship with Pediatric Head Trauma Severity and Outcome, Childs Nerv. Syst., 21, 185-193 (2005) (DOI: 10.1007/s00381-004-1032-1).
Pestka, Sidney, The Interferons: 50 years After Their Discovery, There is Much More to Learn, J. Biol. Chem., 282(28):20047-51 (2007) (DOI:10.1074/jbc.R700004200).
Karve, I.P., et al., Ablation of Type-1 IFN Signaling in Hematopoietic Cells Confers Protection Following Traumatic Brain Injury, eNeuro 3:ENEURO.0128-15.2016, (2016) (DOI:10.1523/ENEURO.0128-15).
Cunha, F.Q., et al., Interleukin-10 (IL-10) Inhibits the Induction of Nitric Oxide Synthase by Interferon-y in Murine Macrophages, Biochemicaland Biophysical. Research Communications, 182(3), pp. 1155-1159 (1992) (DOI: 10.1016/0006-291X(92)91852-H).
Scott, M.J., et al., Interleukin-10 Suppresses Natural Killer Cell but Not Natural Killer T Cell Activation During Bacterial Infection, Cytokine, 33(2):79-86 (2006) (DOI: 10.1016/j.cyto.2005.12.002).
Zhang, L., et al., Lipopolysaccharide Activated Phosphatidylcholine-specific Phospholipase C and Induced IL-8 and MCP-1 Production in Vascular Endothelial Cells, J. Cell. Physiol., 226(6), 1694-1701 (2011) (DOI: 10.1002/jcp.22500).
Bickel, M., The Role of Interleukin-8 in Inflammation and Mechanisms of Regulation, J. Periodontol., 64(5 Suppl): 456-460 (1993) (PMID: 8315568).
Semple, B.D., et al., Role of CCL2 (MCP-1) in Traumatic Brain Injury (TBI): Evidence from Severe TBI Patients and CCL2-/- Mice, J. Cereb. Blood Flow Metab., 30(4): 769-782 (2010) (DOI: 10.1038/cbfm.2009.262).
Kumar, R.G., el al., Chronic Inflammation After Severe Traumatic Brain Injury: Characterization and Associations with Outcome at 6 and 12 Months Post Injury, J. Head Trauma Rehabil., 30(6): 369-381 (2015) (10.1097/HTR.0000000000000067).
Kushi H., et al., L-8 is a Key Mediator of Neuro Inflammation in Severe Traumatic Brain Injuries, Acta Neurochir. Suppl. 86:347-350 (2003) (DOI: 10.1007/978-3-7091-0651-8_74).
Mussack, Thomas, et al., Serum S-IOOB and Interleukin-8 as Predictive Markers for Comparative Neurologic Outcome Analysis of Patients after Cardiac Arrest and Severe Traumatic Brain Injury, Crit. Care Med., 30(12), 2669-2674 (2002) (DOI: 10.1097/00003246-200212000-00010).
Murray, Katie, et al., Interleukin-I and Acute Brain Injury, Front. Cell. Neurosci., 9:18 (2015) (DOI: 10.3389/fncel.2015.00018).
Dardiotis Efthimios, et al., Traumatic Brain Injury and Inflammation: Emerging Role of Innate and Adaptive Immunity. In: Brain Injury—Pathogenesis, Monitoring, Recovery and Management, InTech Europe, Rijeka, Croatia, pp. 23-38 (2012) (DOI:10.5772/27840).
Schneider, Soares F.M., et al., Interleukin-10 is an Independent Biomarker of Severe Traumatic Brain Injury Prognosis, Neuroimmunomodulation, 19(6): 377-385 (2012) (DOI: 10.1159/000342141).
Pike, B.R., et al., Accumulation of Calpain and Caspase-3 Proteolytic Fragments of Brain-Derived Alpha 11-Spectrin in Cerebral Spinal Fluid after Middle Cerebral Artery Occlusion in Rats, J. Cereb. Blood Flow Metab., 24:98-106 (2004) (10.1097/01.WCB.0000098520.11962.37).
Wang, K. K., Proteomic Identification of Biomarkers of Traumatic Brain Injury, Expert Rev. Proteomics, 2(4):603-614 (2005) (DOI: 10.1586/14789450.2.4.603).
Schiavone S., et al., The NADPH Oxidase NOX2 Mediates Loss of Parvalbumin Interneurons in Traumatic Brain Injury: Human Autoptic Immunohistochemical Evidence, Sci. Rep., 7(1):8752 (2017) (DOI: 10.1038/s41598-017-09202-4).
Ziu, M., et al., Temporal Differences in MicroRNA Expression Patterns in Astrocytes and Neurons after Ischemic Injury, PLoS One., 23;6(2):e14724 (2011) (DOI:10.1371/journal.pone.0014724).
Palmer A.M., et al., Traumatic Brain Injury-induced Excitotoxicity Assessed in a Controlled Cortical Impact, Model, J. Neurochem., 61:2015-2024 (1993) (DOI: 10.1111/j.1471-4159.1993.tb07437.x).
Oasis Diagnostics Our Products, https://4saliva.com/products/, Oasis Diagnostics Corporation, Vancouver, WA 98686, Downloaded from the Internet Apr. 2, 2020.
Infectious Disease Testing, www.orasure.com/products-infectious/index. html, OraSure Technologies, Inc., Bethlehem, PA 18015, Downloaded from the Internet Dec. 3, 2020.
OraQuick Advance HIV, www.orasure.com/products-infectious/OraQuick-Advance-HIV/html, OraSure Technologies, Inc., Bethlehem, PA 18015, Downloaded from the Internet Dec. 3, 2020.
Aaron Dadas et al.: Biomarkers in traumatic brain injury (TBI): a review, Neuropsychiatric Disease and Treatment, vol. 14, Nov. 1, 2018 (Nov. 1, 2018), pp. 2989-3000, XP005671723, DOI: 10.2147/NDT.S125620 (p. 2997, col. 1, para 1 to col. 2, para 1)(p. 2990, col. 2, para 1).
Jacqueline R. Kulbe et al.: "Current status of fluid biomarkers in mild traumatic brain injury", Experimental Neurology, vo. 275, May 14, 2015 (May 14, 2015), pp. 334-352, XP055538030, Amsterdam, NL ISSN: 0014-4886, DOI: 10.1016/j.expneurol.2015.05.004 (p. 6, para 3)(p. 9, para 1 ff)(p. 10, para 3 ff) (p. 12, para 3 ff).

(56) References Cited

OTHER PUBLICATIONS

Caswell S V et al: "Development of Nanoparticle-Enabled Protein Biomarker Discovery: Implementation for Saliva-Based Traumatic Brain Injury Detection", Advances in Salivary Diagnostics, Springer, Berlin, Heidelberg, pp. 121-129, Feb. 20, 2015 (Feb. 20, 2015), XP009519060, ISBN: 978-3-662-45398-8 Retrieved from the Internet: URL:https://ebookcentral.proquest.com/lib/epo-ebooks/reader.action?docID=1964558&ppg=132 [retrieved on Jan. 3, 2015].

PCT/IN2019/050864 International Search Report and Written Opinion of the International Searching Authority, Mar. 11, 2020.

* cited by examiner

METHODS, SYSTEMS, AND A KIT FOR DIAGNOSIS, DETECTION, MONITORING AND TREATMENT OF TRAUMATIC BRAIN INJURY

RELATED APPLICATION

This application is a national stage application under 35 U.S.C. § 371 of International Application No. PCT/IN2019/050864, filed Nov. 25, 2019, which claims the benefit and priority date of Indian patent application Ser. No. 20/181,1044520 filed Nov. 26, 2018, the entire contents of which are incorporated herein by reference for continuity.

FIELD OF THE INVENTION

The invention relates to saliva-based diagnostics and treatment of concussion and traumatic brain injury, including mild traumatic brain injury. The invention further relates to methods for detecting, diagnosing, monitoring, and treating concussion and traumatic brain injury, including mild traumatic brain injury.

BACKGROUND OF THE INVENTION

Considerable importance is placed on the mental and physical well-being and social growth of adolescents and young adults, including those who participate in athletics. Sport-related injuries are an important risk in this population because contact sports such as football, hockey, etc. carry a risk of brain injury. Therefore, sport-related concussions and related injuries are an important public health issue.

According to the Center for Disease Control and Prevention (CDC), it is estimated that 1.6 to 3.8 million sport-related concussion injuries occur annually. Concussions are also referred to herein by the term "mild traumatic brain injury", abbreviated as "mTBI". Traumatic brain injuries generally are referred to herein by the abbreviation "TBI". (Coronado V G, Haileyesus T, Cheng T A, Bell J M, Haarbauer-Krupa J, Lionbarger M R, Flores-Herrera J, McGuire L C, Gilchrist J, Trends in Sports- and Recreation-Related Traumatic Brain Injuries Treated in US Emergency Departments: The National Electronic Injury Surveillance System-All Injury Program (NEISS-AIP) 2001-2012. J. Head Trauma Rehabilitation 2015; 30 (3): 185-197.) In rugby, concussion can affect as many as 40% of players on a team each year. TBIs result in approximately 30% of all injury deaths. (Taylor C A, Bell J M, Breiding M J, Xu L., Traumatic Brain Injury—Related Emergency Department Visits, Hospitalizations, and Deaths—United States, 2007 and 2013. MMWR Surveill Summ 2017; 66 (No. SS-9): 1-16.) Repeated concussions present a considerable threat to the long-term health of the individual. The healthcare costs linked with mTBI in sports are predicted to be in the hundreds of millions of dollars yearly.

Concussion is linked to adverse effects within the first week post-injury, including physical complaints and altered cognition, sleep and mood. These changes as tools are useful in tracking recovery post-injury, but these tests are very subjective. Few patients are reported to have treatment for mTBI and the diagnosis of mTBI represents a noteworthy challenge. Diagnosis to date has been subjective and frequently based on self-reported neurological symptoms, some of which could be ignored, concealed, or overstated. Appropriate actions in both pre-hospital and early in-hospital stays should be implemented as significant factors in decreasing mortality and in the recovery of the patient's neurological outcome. (Taylor C A, Bell J M, Breiding M J, Xu L., Traumatic Brain Injury—Related Emergency Department Visits, Hospitalizations, and Deaths—United States, 2007 and 2013. MMWR Surveill Summ 2017; 66 (No. SS-9):1-16.)

Serum or blood concentrations of the proteins Calcium Binding Protein B (5-100β) and Maltose Binding Protein (MBP) correlate with the severity of TBI, but detection of these biomarkers require invasive techniques and specific training is needed for analysis of these biomarkers. (Rodriguez-Rodriguez A, Egea-Guerrero J J, León-Justel A, Gordillo-Escobar E, Revuelto-Rey J, Vilches-Arenas A, Carrillo-Vico A, Dominguez-Roldan J M, Murillo-Cabezas F, Guerrero J M, Role of S100β Protein in Urine and Serum as an Early Predictor of Mortality After Severe Traumatic Brain Injury in Adults. Clin Chim Acta. 2012; 414:228-33. doi: 10.1016/j.cca.2012.) And recently, two brain-specific protein biomarkers, Glial Fibrillary Acidic Protein and Ubiquitin Carboxy-terminal Hydrolase-L1 in blood, were approved by the United States Food and Drug Administration (FDA), but this test is invasive in nature, so there are no non-invasive, cost effective and real time, user-friendly tests for detection of mTBI in a subject.

Thus, the above-mentioned issues together indicate that it is specifically in mTBI patients, in whom clinical diagnosis is difficult, that a laboratory-based test, point-of-care test, or other non-invasive tests have the greatest prospect for therapeutic intervention. To date, no reliable laboratory-based test, point-of-care test, or other non-invasive tests for detection and diagnosis of mTBI exist, particularly in the early stages of mTBI. So, there is an urgent requirement for a method of pre-symptomatic diagnosis of mTBI, a method for the diagnosis of symptomatic mTBI, a method of evaluating the risk of developing mTBI, and of estimating the prognosis of a treatment of mTBI through a laboratory, point-of-care, field kit, mobile phone or smart kit, etc., based test. Such diagnostic capability would provide physicians, team coaches, and others with objective tools for the diagnosis and treatment of patients who have sustained mTBI, including subjects in the adolescent, young adult, and older populations. There is a clinical need for salivary biochemical marker tests that can be used as an aid in the diagnosis of head injury, as potential tools in patient stratification, early detection, screening, monitoring, and as prognostic aids in helping predict the patient outcome, especially among patients suffering from mild TBI.

SUMMARY

The invention relates to methods for improving the diagnosis and treatment of head injuries in order to minimize and/or eliminate the adverse effects of head trauma in patients.

Provided herein is a non-invasive means for detecting, measuring, diagnosing, treating and monitoring different types of traumatic brain injuries (TBI); e.g., mild concussion (mTBI), and moderate and severe traumatic brain injury (TBI), by means of salivary biomarkers.

A mild traumatic brain injury (mTBI) that occurs in sports is principally referred to as a concussion. A concussion can cause changes in the structure of a brain which leads to downstream cognitive problems and increases the risk of depression. Mild, moderate, and severe TBI depend on a number of different factors including the type of injury (diffuse or local), the extension and location of the injury, and the type of injury, etc.

The Glasgow Coma Scale is a commonly used indictor to estimate the level of TBI. (Teasdale G, Jennett B., Assessment of Coma and Impaired Consciousness. A practical scale. Lancet 1974; 2:81-84.) It is based on the score for best motor and verbal response as well as minimum stimulus to cause eye opening. (Severe Level: 3 to 8, Moderate Level: 9 to 12, and Mild Level: 13 to 15, according to the Advanced Trauma Life Support (ATLS), American College of Surgeons Committee on Trauma, Chicago, Illinois 2004.) The clinical assessment of sport-related concussion has been standardized with the development of the Sport Concussion Assessment Tool (SCAT), which has shown diagnostic utility for acute concussions. (Echemendia R J, Broglio S P, Davis G A, Guskiewicz K M, Hayden K A, Leddy J J, Meehan W P, Putukian M, Sullivan S J, Schneider K J., What Tests and Measures Should be Added to the SCAT3 and Related Tests to Improve their Reliability, Sensitivity and/or Specificity in Sideline Concussion Diagnosis? A Systematic Review. Br. J. Sports Med. 2017; 51:895-901.)

As disclosed herein, one or multiple biomarkers in the bodily fluids of an individual might be quantitatively measured alone or in combination for the detection, diagnosis and treatment of traumatic brain injury, such as mild, moderate, and severe TBI. Levels of biomarkers may also be used to monitor the progression and severity of mild, moderate, and severe traumatic brain injury (TBI) and to determine the effectiveness of a particular treatment in arresting or reversing the progression of these disorders.

Biomarkers as used herein may be one or more of Neuron Specific Enolase (NSE), Glial Fibrillary Acidic Protein (GFAP), Ubiquitin Carboxy-Terminal Hydrolase L1 (UCH-L1), Interleukin-1β (IL-1β), Interferon Gamma (IFN-γ), Interleukin 8 (IL-8), Interleukin 10 (IL-10), Spectrin II, and/or 8-Hydroxy-2'-Deoxyguanosine (8-OHdG.) The methods described herein comprise the identification of biomarkers such as proteins, and genetic and transcriptomic biomarkers in a biological fluid, such as saliva. Such biomarkers may be identified by any means generally used by one a skill in the art.

In some embodiments, these biomarkers are identified using antibody-based methods, such as, but not limited to, an enzyme-linked immunosorbent assay (ELISA), a radioimmunoassay (RIA), an antibody based assay, western blotting, mass spectrometry, microarray, protein microarray, flow cytometry, immunofluorescence, PCR, aptamer-based assay, immunohistochemistry, a multiplex detection assay, a lateral flow immunoassay, or exosomes, a point-of-care and field kit, mobile phone or smart kit, and proteomic approaches that utilize various detection methods. All of the foregoing are types and examples of measurement devices useful to detect the biomarkers according to the invention.

In another aspect, this invention comprises a system of diagnosing, screening, early detection, prognosis, and treatment of mild concussion (mTBI), moderate, and severe traumatic brain injury (TBI) by using computer-readable media which consists of a computer-readable program code, including instructions for performing the diagnosis. The system consists of an assay (i.e., a measuring device) for estimating the test level of one or a set of biomarkers, computer hardware, and a software program stored in computer-readable media or smart technologies including a smart mobile device such as an iPhone, an iPad, etc., extracting the test level from the assay, diagnosis, detection and treatment of the subject having mild concussion (mTBI), or moderate or severe traumatic brain injury according to reference levels and concentration of biomarkers, the result of which show whether the subject is having a mild concussion, or moderate or severe traumatic brain injury.

In still another aspect, the present invention includes a kit for the diagnosis of mild concussion (mTBI), and moderate to severe traumatic brain injury (TBI.) The kit consists of testing reagents for one or a set of biomarkers and instructional material for use thereof.

In yet another aspect, this invention additionally provides a kit for the diagnosis, monitoring, prognosis, treatment, and detection of mild concussion (mTBI), and moderate to severe traumatic brain injury (TBI.) The kit consists of: (a) a panel of any one or two, more than two, all, or more of the above-identified biomarkers; (b) a substrate for holding a biological sample isolated from a human subject suspected of a mild concussion (mTBI), or moderate, or severe traumatic brain injury (TBI), etc., or being under treatment or intervention for mild concussion (mTBI) or moderate, or severe traumatic brain injury (TBI); (c) an agent which connects or binds to at least one of the biomarkers; (d) a measurable label; i.e., one conjugated to the agent, or one conjugated to a substance which specially binds at least to one or more of the biomarkers and presents a proportional reaction based on the level of biomarker present, (e) a measurement device operable to indicate the measurable label to provide a qualitative or quantitative level of one or more biomarkers in the saliva sample indicative that the subject has mTBI and (f) printed or computer based, or e-printed, or remote instructions for reacting the agent with the biological sample, or a portion of the biological sample, to detect the presence or concentration of at least one biomarker in the biological sample and estimating if the biomarker is within a reference level of the biomarker.

In other embodiments, the kits are used within the same time-of-day window in a similar way and/or with the same test used to estimate the reference levels of the biomarker.

Additionally, in the other embodiments, the time between when the saliva sample is taken and when the subject may have sustained an injury to the head might not be known. Otherwise, the time between when the saliva sample is taken and when the subject might have sustained an injury to the head might be selected from the group of from zero to about 12 hours, from about 12 to about 24 hours, from about 24 to about 36 hours, from about 36 to about 48 hours, from about 48 to about 72 hours, from about 72 to about 96 hours, from about 96 to about 120 hours, from about 120 hours to about 7 days, from about 7 days to about 1 month, from about 1 month to about 3 months, from about 3 months to about 6 months, from about 6 months to about 1 year, from about 1 year to about 3 years, from about 3 years to about 6 years, from about 6 years to about 12 years, from about 12 years to about 20 years, from about 20 years to about 30 years, and from about 30 years to about 50 years. Alternatively, the time between when the biological sample is obtained and when the subject may have sustained an injury to the head may be selected from the group consisting of less than 50 years, less than 30 years, less than 20 years, less than 12 years, less than 6 years, less than 3 years, less than 1 year, less than about 6 months, less than about 3 months, less than about 1 month, less than about 7 days, less than about 120 hours, less than about 96 hours, less than about 72 hours, less than about 48 hours, less than about 36 hours, less than about 24 hours, or less than about 12 hours.

In the above methods, a saliva sample can be taken after the subject may have sustained an injury to the head caused by physical shaking, by blunt impact, by an external mechanical or other force that results in a closed or open head trauma, by one or more falls, explosions or blasts, or by other types of blunt force trauma.

In yet another aspect, a biomarker or a panel of biomarkers, may be integrated into a mouth guard to estimate the extent of injury even before medical personnel see the patient, thus saving time, reducing cost, and reducing exposure to radiation.

In still another aspect, the invention includes compositions, methods and uses of a novel set of biomarkers to assess the risk, screening, diagnosis, treatment, detection, as well as monitoring of mild concussion (mTBI) and moderate to severe traumatic brain injury (TBI) and to estimate the prognosis of concussion and traumatic brain injury such as mild, moderate, severe TBI, following therapeutic or other treatment and intervention. The set of biomarkers consists of at least NSE, GFAP, UCH-L1, IL-1β, IFN-γ, IL-8, IL-10, Spectrin II, and/or 8-OHdG.

In another embodiment, the reference levels for biomarkers are established based on biomarker levels in a sample taken from a subject at a previous point in time. The subject is estimated to be reacting to treatment, intervention, and management for mild concussion (mTBI), or moderate to severe traumatic brain injury (TBI), etc., if levels of the biomarkers in the biological sample, especially in saliva, have altered positively (e.g., increased) from the biomarker levels in a biological sample taken at an earlier time point from the same subject.

These and other embodiments and specific and possible advantages will become evident with reference to the following description.

DETAILED DESCRIPTION

Traumatic brain injury (TBI) can occur when a sudden, violent blow or jerk to the head leads to damage to the brain. In the United States and elsewhere, TBI is a major cause of disability and death, including to adolescent and young adult athlete populations. As the brain collides with the inside of the skull, there might be bruising of the brain, tearing of nerve fibers and bleeding. If the skull fractures, a broken piece of skull might enter into the brain tissue. Causes of TBI are not limited to sports-related injuries and comprise falls, gunshot wounds, physical aggression, and road and traffic accidents.

The Centers for Disease Control and Prevention (CDC) define a TBI as "a disruption in the normal function of the brain that can be caused by a bump, blow, or jolt to the head, or penetrating head injury." Symptoms of TBI can vary from mild, to moderate, to severe. There may or may not be a loss of consciousness. Different symptoms of mTBI are headaches, confusion, lightheadedness, dizziness, blurred vision, tinnitus, dysgeusia, fatigue, changes in sleep patterns or behavior, and impairment of memory or cognition.

Despite the existence of variable clinical presentations, patients with mTBI are analyzed or detected clinically by experts only. Normally, a Glasgow Coma Scale (GCS) score of 13-15 defines mild traumatic brain injury (mTBI.) There is no ideal test. Furthermore, lack of tests for detection, diagnosis, and treatment of mTBI and also for moderate, or severe traumatic brain injury, etc. is one of the hindrances in the development of new treatments. The difficulty in exactly diagnosing mild concussion (mTBI) and moderate or severe traumatic brain injury (TBI), etc. furthermore leads to high rates of misdiagnosis or improper diagnosis, negatively effecting families and delaying or preventing treatment for mild concussion (mTBI) and for moderate to severe traumatic brain injury (TBI.)

The detection of appropriate biomarkers and combinations of biomarkers useful for predicting, diagnosing, prognosis, treating, and monitoring mild concussion (mTBI), moderate TBI, and severe traumatic brain injury (TBI) are described herein. Biomarkers are helpful for diagnosing early stage mild concussion (mTBI), and moderate to severe traumatic brain injury (TBI) enabling earlier treatment options. Furthermore, the biomarkers disclosed herein may be used as drug targets to develop new drugs, as well as to monitor different therapies for the treatment and management of mild concussion (mTBI) and moderate to severe traumatic brain injury (TBI.)

In terms of the classification of severity, traditionally TBI has been classified as mild, moderate, or severe by using the Glasgow Coma Scale, a system used to evaluate coma and impaired consciousness. The Glasgow Coma Scale is divided into three components—eye opening, verbal response, and motor responses. These are typically summed to produce a total score. A Glasgow Coma Scale score of 13-15 is defined as mild, 9-12 as moderate, and a score of 3-8 is defined as severe. (Teasdale, G, Jennett, B. Assessment of Coma and Impaired Consciousness. A practical Scale. Lancet.1974; 304(7872):81-84.)

"Evaluate", "diagnosis", "determinant", "found", "discriminate", "detection" and "establish" are interchangeably used for diagnosis.

"Subject" and "individual" are interchangeably when used for a human individual.

As used herein, the terms "comprising", "including", "containing", "composition", "consisting", and "characterized by" are interchangeable, inclusive, open-ended and do not exclude additional, methods or procedural steps.

The terminology used herein is for the purpose of describing specific embodiments only and is not intended to be limiting of the invention. As used in this document, the singular forms "a,", "an", and "the" include plural references unless the context clearly dictates otherwise. Unless defined otherwise, all technical and scientific terms used herein have the same meanings as commonly understood by one of normative skill in the art.

"Detecting", "measuring", or "taking a measurement" define a quantitative or qualitative determination of the amount, or level, or concentration of the biomarker in the sample. A measurement device operable to provide a qualitative or quantitative level of one or more biomarkers in the sample may be implemented.

As used herein, the terms "treatment", "therapeutic effect", "therapeutic activity", or "therapeutic action" refer to the mitigation, amelioration, and/or stabilization of symptoms and signs, as well as a delay in the progression of symptoms and signs of a particular disorder, through the use of some external drug, device, technology, or other technique.

As used herein, a "reference value" of a biomarker is a relative value, an absolute value, a range of values, a value that has an upper and/or lower limit, an average value, a median value, a mean value, a value as compared to a control or baseline value, or a combination thereof.

As used herein, a "time-of-day window", when referring to times in which samples are taken, means a period of time defined via a window start time and a window stop time.

As used herein, "biomarker panel" defines a set of biomarkers used alone, in combinations, or in sub-combinations for the detection, diagnosis, prognosis, treatment, or monitoring of a disease or condition based on detection values for the set of biomarkers. The biomarkers within the panel of biomarkers used herein include NSE, GFAP, UCH-L1, IL-1β, IFN-γ, IL-8, IL-10, Spectrin II, and/or 8-OHdG.

Neuron Specific Enolase (NSE) is a glycolytic enzyme that converts 2-phosphoglycerate to phosphoenolpyruvate. The protein is enriched in neuronal cell bodies, but is also found in neuroendocrine cells, oligodendrocytes, blood platelets, and at particularly high concentrations in erythrocytes. (Schmechel D, Marangos P J & Brightman M., Neurone-Specific Enolase is a Molecular Marker for Peripheral and Central Neuroendocrine Cells. Nature. 1978; 276: 834-836; Dash P K, Zhao J, Hergenroeder G & Moore A N., Biomarkers for the Diagnosis, Prognosis, and Evaluation of Treatment Efficacy for Traumatic Brain Injury. Neurotherapeutics 2010; 7:100-114.) Different studies have examined NSE in serum as a potential biomarker for mTBI. Initial results were promising showing increased serum NSE concentrations in samples taken from patients with mTBI within a few hours post-injury, but when scrutinizing the data, the overlap with non-concussed controls makes the diagnostic utility uncertain (Skogseid I M, Nordby H K, Urdal P, Paus E & Lilleaas F. Increased serum Creatine Kinase BB and Neuron Specific Enolase following head injury indicates brain damage. (Acta Neurochir (Wien.) 1992; 115:106-111.) These technologies are invasive, need specific training to perform the sampling, cannot be performed in real time (e.g., immediately or shortly after the suspected injury, such as at an athletic event), and are relatively expensive. Accordingly, there is a need for an urgent technology which is noninvasive, easy to use, can be implemented in real time, and is cost effective as accomplished by the present invention.

Glial Fibrillary Acidic Protein (GFAP) is the main constituent of intermediate filaments of the cytoskeleton of astrocytes. (Gill J, Latour L, Diaz-Arrastia R, Motamedi V, Turtzo C, Shahim P, Mondello S, DeVoto C, Veras E, Hanlon D, Song L, Jeromin A., Glial Fibrillary Acidic Protein Elevations relate to Neuroimaging Abnormalities after Mild TBI. Neurology. 2018; 91(15):e1385-e1389.) GFAP acts as a classical marker for astroglia. The main functions of GFAP are the maintenance of specific morphology of astrocytes, management of migration of these cells, and upholding of the stability of their processes. GFAP is also involved in the processes of cellular signaling and modulation of neuron-to-glia interactions. (Gardner R C, Rubenstein R, Wang K K W, Korley F K, Yue J K, Yuh E L, Mukherje P, Valadka A B, Okonkwo D O, Diaz-Arrastia R, Manley G. Age-Related Differences in Diagnostic Accuracy of Plasma Glial Fibrillary Acidic Protein and Tau for Identifying Acute Intracranial Trauma on Computed Tomography: A TRACK-TBI Study. J. Neurotrauma. 2018; 35(20):2341-2350.) GFAP is a promising marker of brain injury in patients with acute mTBI. (Gill J, Latour L, Diaz-Arrastia R, Motamedi V, Turtzo C, Shahim P, Mondello S, DeVoto C, Veras E, Hanlon D, Song L, Jeromin A., Glial Fibrillary Acidic Protein Elevations Relate to Neuroimaging Abnormalities after Mild TBI. Neurology. 2018; 91(15):e1385-e1389.) GFAP might be a promising diagnostic tool for children with mTBI. (Rhine T, Babcock L, Zhang N, Leach J, Wade S L., Are UCH-L1 and GFAP Promising Biomarkers for Children with Mild Traumatic Brain Injury? Brain Inj. 2016; 30(10): 1231-8; US20180106818; 10041959.) These technologies are invasive, need specific training in order to be capable of performing the sampling, cannot be provided in real time (e.g., immediately or shortly after the suspected injury, such as at an athletic event), and are relatively expensive. Accordingly, there is a need for an urgent technology which is noninvasive, easy to use, can be implemented in real time, and is cost effective as accomplished by the present invention.

Ubiquitin Carboxy-terminal Hydrolase L1 (UCH-L1) is an enzyme present in the soma of neurons. Higher circulating levels of UCH-L1 has been found in non-survivor, compared to survivor, TBI patients. (Mondello S, Linnet A, Buki A, Robicsek S, Gabrielli A, Tepas J, Papa L, Brophy G M, Tortella F, Hayes R L, et al., Clinical Utility of Serum Levels of Ubiquitin C-Terminal Hydrolase as a Biomarker for Severe Traumatic Brain Injury. Neurosurgery. 2012; 70:666-675; Ost M, Nylén K, Csajbok L, Ohrfelt A O, Tullberg M, Wikkelso C, Nellgard P, Rosengren L, Blennow K, Nellgard B., Initial CSF Total Tau Correlates with 1-year Outcome in Patients with Traumatic Brain Injury. Neurology. 2006; 67:1600-1604) and might be the expression of neuron damage. UCH-L1 was identified as a protein with a two-fold increase in abundance in the injured cortex 48 hours after controlled cortical impact in a rat model of TBI. (Liu M C, Akinyi L, Scharf D, et al., Ubiquitin C-terminal Hydrolase-L1 as a Biomarker for Ischemic and Traumatic Brain Injury in Rats. Eur J. Neurosci. 2010; 31(4):722-732; U.S. Patent Publication Nos. 2018/0313837 and 2009/0208508.) These technologies are invasive, need specific training in order to perform the sampling, cannot be performed in real time (e.g., immediately or shortly after the suspected injury, such as at an athletic event), and are relatively expensive. Accordingly, there is an urgent need for technology which is noninvasive, easy to use, can be performed in real time, and is cost effective as can be accomplished by means of the present invention.

Interleukin 1 Beta (IL-1β) is a regulated, potent pro-inflammatory cytokine which is released by macrophages and monocytes. (Quagliarello V J, Wispelwey B, Long W J Jr., Scheld W M, Recombinant Human Interleukin-1 Induces Meningitis and Blood-Brain Barrier Injury in the Rat. Characterization and Comparison with Tumor Necrosis Factor. J. Clin. Invest. 1991; 87(4): 1360-6.) Various studies have reported an acute global increase in IL-1β mRNA, protein and activated Caspase-1 in postmortem brain tissue following TBI. (Frugier T, Morganti-Kossmann MC, O'Reilly D, McLean CA., In Situ Detection of Inflammatory Mediators in Post-Mortem Human Brain Tissue After Traumatic Injury. J. Neurotrauma 2010; 27(3): 497-507.) Nevertheless, many more contradictory findings have been observed regarding IL-1β levels in serum and CSF, with different studies reporting weak or no linked in severe TBI. (Singhal A, Baker A J, Hare G M, Reinders F X, Schlichter L C, Moulton R J, Association Between Cerebrospinal Fluid Interleukin-6 Concentrations and Outcome after Severe Human Traumatic Brain Injury. J. Neurotrauma 2002; 19(8):929-937.) But there is other reporting of a significant increase in IL-1β following severe TBI. (Buttram S D, Wisniewski S R, Jackson E K et al., Multiplex Assessment of Cytokine and Chemokine Levels in Cerebrospinal Fluid Following Severe Pediatric Traumatic Brain Injury: Effects of Moderate Hypothermia. J. Neurotrauma 2007; 24(11): 1707-1718.) High CSF and serum concentrations of IL-1β have been linked with poorer 3- and 6-month outcomes as well as increased ICP following severe head trauma. (Tasçi A, Okay Ö, Gezici A R, Ergün R, Ergüngör F, Prognostic Value of Interleukin-1 Beta Levels After Acute Brain Injury. Neurol. Res. 2003; 25(8): 871-874; Chiaretti A, Genovese O, Aloe L et al., Interleukin 1β and Interleukin 6 Relationship with Pediatric Head Trauma Severity and Outcome. Childs Nerv. Syst. 2005; 21(3): 185-193; U.S. Patent Publication No. 2013/0121962 and U.S. Pat. No. 6,974,809.) These technologies are invasive, require training in order to be properly implemented, are not suited to be performed in real time (e.g., immediately or shortly after the suspected injury, such as at an athletic event.) There is an urgent need for technology which is noninvasive, easy to use, can be performed in real time, and is cost effective such as can be implemented with the present invention.

Interferons (IFNs) have been known as autocrine or paracrine factors secreted through a large number of eukaryotic cells in response to viral infections, with the capability to effectively confine the spreading of viruses. (Pestka S. The Interferons: 50 years After Their Discovery, There is Much More to Learn. J. Biol. Chem.2007; 282:20047-51. 10.1074/jbc.R700004200.) The expression of IFN-α, IFN-β, and IFN-γ has been observed in biological samples of human patients, including brain microdialysate, brain tissue, and cerebrospinal fluid (CSF.) (Karve I P, Zhang M, Habgood M, Frugier T, Brody K M, Sashindranath M, et al., Ablation of Type-1 IFN Signaling in Hematopoietic Cells Confers Protection Following Traumatic Brain Injury. eNeuro (2016) 3: ENEURO.0128-15.2016. 10.1523/ENEURO.0128-15.) A significant fraction of investigations has indicated on validating IFNs as prognostic or diagnostic markers. (Cunha F Q, Mohcada S, Liew F Y.) Interleukin-10 (IL-10) inhibits the induction of nitric oxide synthase by Interferon-γ in murine macrophages. (Biochem. Biophys. Res. Commun. 1992; 182(3), 1155-1159.) The main focus has been on IFN-γ because of its well-known role in lymphocyte-driven inflammation. However, the recent appreciation of the role of type-I IFNs in inflammation, beyond viral infections, has led to the assessment of type-I IFNs in neurotrauma. (U.S. Patent Publication No. 2015/0239951 and U.S. Pat. No. 6,911,198.) These technologies are invasive, require training in order to be properly implemented, and are not suited to be performed in real time (e.g., immediately or shortly after the suspected injury, such as at an athletic event). There is an urgent need for technology which overcomes these problems such as can be implemented with the present invention.

Interleukin-8 (IL-8) is a member of a special class of small cytokines known as chemokines. It is secreted by different cells such as glial cells, macrophages and endothelial cells. (Scott M J, Hoth J J, Turina M, Woods D R, Cheadle W G, Interleukin-10 Suppresses Natural Killer Cell but Not Natural Killer T Cell Activation During Bacterial Infection. Cytokine 2006; 33(2):79-86.) IL-8 is released from astrocytes in the presence of other cytokines that are acutely expressed following a TBI, such as TNF or IL-1β. (Zhang L, Li H Y, Li H et al. Lipopolysaccharide Activated Phosphatidylcholine-specific Phospholipase C and Induced IL-8 and MCP-1 Production in Vascular Endothelial Cells. J. Cell. Physiol. 2011; 226(6), 1694-1701.) IL-8 induces chemotaxis and phagocytosis of neutrophils, attracting them to the site of neural damage and cleanup debris leading from the injury. (Bickel M. The Role of Interleukin-8 in Inflammation and Mechanisms of Regulation. J. Periodontol.1993; 64(Suppl. 5): 456-460.) While neutrophils classically leave the brain by 1 week subsequent a brain injury, macrophages have been reported to linger for approximately 4 weeks. (Semple B D, Bye N, Rancan M, Ziebell J M, Morganti-Kossmann M C, Role of CCL2 (MCP-1) in Traumatic Brain Injury (TBI): Evidence from Severe TBI Patients and CCL2−/− Mice. J. Cereb. Blood Flow Metab. 2010; 30(4): 769-782.) This prolonged presence of activated leukocytes in the brain is neurotoxic and has been suggested to contribute to the ongoing neuronal damage that occurs following the acute brain injury. In addition to several other pro-inflammatory cytokines, different studies have reported both acute and persistent increases in IL-8 levels following severe TBI. (Kumar R G, Boles J A, Wagner A K. Chronic Inflammation After Severe Traumatic Brain Injury: Characterization and Associations with Outcome at 6 and 12 Months Post injury. J. Head Trauma Rehabil. 2015; 30(6): 369-381.) The greatest increases in IL-8 concentrations are observed in CSF. (Kushi H, Saito T, Makino K, Hayashi N, L-8 is a Key Mediator ofNeuro Inflammation in Severe Traumatic Brain Injuries. Acta Neurochir. Suppl. 2003; 86:347-350.) IL-8 concentrations have also been observed to a lesser degree in serum after severe injuries. (Mussack T, Biberthaler P, Kanz K G et al. Serum S-100B and Interleukin-8 as Predictive Markers for Comparative Neurologic Outcome Analysis of Patients after Cardiac Arrest and Severe Traumatic Brain Injury. Crit. Care Med. 2002; 30(12), 2669-2674.) Once again, these technologies are invasive, require training in order to be properly implemented, and are not suited to be performed in real time (e.g., immediately or shortly after the suspected injury, such as at an athletic event). There is an urgent need for technology which overcomes these problems such as can be implemented with the present invention.

Interleukin 10 (IL-10) has an inhibitory effect on the production of numerous pro-inflammatory mediators, eventually serving to regulate many of the cytokines which have been linked to acute and chronic inflammatory processes. Chiefly relevant to inflammation following severe TBI is its effect of IL-10 on IL-1β and TNF, and interferon (IFN), all of which have been observed to cause detrimental effects on the brain. (Murray K N, Parry-Jones A R, Allan S M, Interleukin-1 and Acute Brain injury. Front. Cell. Neurosci. 2015; 9:18.) IL-10 expression appears to increase within the first 24 hours following a severe head trauma. (Dardiotis E, Karanikas V, Paterakis K, Fountas K, Hadjigeorgiou G M, Traumatic Brain Injury and Inflammation: Emerging Role of Innate and Adaptive Immunity. In: Brain Injury—Pathogenesis, Monitoring, Recovery and Management. Agrawal A, InTech, Rijeka, Croatia, 2012; 23-38.) Consistent with anti-inflammatory properties, this increase in IL-10 has been reported to correspond with a decrease in TNF levels. Though, despite this well-documented anti-inflammatory role of IL-10, increased IL-10 following TBI has been repeatedly linked to poor outcome and mortality in both pediatric and adult severe TBI. (Schneider Soares F M, Menezes de Souza N, Libório Schwarzbold M et al., Interleukin-10 is An Independent Biomarker of Severe Traumatic Brain Injury Prognosis. Neuroimmunomodulation 2012; 19(6): 377-385.) Significant increases in IL-10 levels are found in non-survivors with severe TBI relative to survivors of the injury. As with the other technologies, these technologies based on IL-10 are invasive, require training in order to be properly implemented, and are not suited to be performed in real time (e.g., immediately or shortly after the suspected injury, such as at an athletic event). There is an urgent need for technology which overcomes these problems such as can be implemented with the present invention.

αII-Spectrin breakdown products (SBDPs) may be potential biomarkers for brain injury in rats and humans. (Pike B. R. Flint J. Dave J. R. LuX. C. Wang K. K. Tortella F. C. Hayes R. L., Accumulation of Calpain and Caspase-3 Proteolytic Fragments of Brain-Derived Alpha II-Spectrin in Cerebral Spinal Fluid after Middle Cerebral Artery Occlusion in Rats. J. Cereb. Blood Flow Metab. 2004; 24:98-106; Wang K. K. Ottens A. K. Liu M. C. Lewis S. B. Meegan C. Oli M. W. Tortella F. C. Hayes R. L., Proteomic Identification of Biomarkers of Traumatic Brain Injury. Expert Rev. Proteomics. 2005; 24:603-614.) αII-spectrin is primarily established in neurons, and is profuse in axons and presynaptic terminals and the protein is processed to breakdown products (SBDP) of molecular weights 150 kDa (SBDP150) and 145 kDa (SBDP145) through calpain, and is also cleaved to a 120-kDa product (SBDP120) by caspase-3. Calpain-mediated necrotic oncosis may play a greater role in acute pathological responses to TBI than caspase-3-mediated apoptosis. But again, these technologies are invasive, require that personnel be trained in order to properly perform the needed sampling, essentially cannot be performed in real time immediately or shortly after the suspected injury and, once again, are relatively expensive. These are problems which are solved by iterations of the present invention.

8-hydroxy-2'-deoxyguanosine (8-OHdG) is one of the major products of DNA oxidation. Concentrations of 8-OHdG within cell are a measurement of oxidative stress. (Schiavone S, Neri M, Trabace L, Turillazzi E. The NADPH Oxidase NOX2 Mediates Loss of Parvalbumin Interneurons in Traumatic Brain Injury: Human Autoptic Immunohistochemical Evidence. Sci. Rep. 2017; 7:8752.) The selection of miRNAs candidates was made by searching in available literature for traumatic brain injury-specific miRNAs which should also be expressed post mortem. The vast majority of scientific reports dealing with traumatic brain injury employs murine models. (Ziu M, Fletcher L, Rana S, Jimenez D F, Digicaylioglu M, Temporal Differences in MicroRNA Expression Patterns in Astrocytes and Neurons after Ischemic Injury. PLoS One. 2011; 6: e14724.) Increased production of highly reactive can also damage DNA, in addition to direct neurotoxic action due to lipoperoxidation and consequent neuronal membrane damage. (Palmer A M. et al. Traumatic Brain Injury-induced Excitotoxicity Assessed in a Controlled Cortical Impact Model. J. Neurochem. 1993; 61:2015-2024.) Technologies based on 8-OHdG are invasive, require training in order to be properly implemented, and are not suited to be performed in real time (e.g., immediately or shortly after the suspected injury, such as at an athletic event). There is an urgent need for technology which overcomes these problems such as can be implemented with the present invention.

Contrasting recently reported tests, which utilized proteins released from damaged neurons or glia and others cells or tissues, etc., the diagnostic test described herein, for concussion (i.e., mTBI), was developed based on a novel combination of salivary biomarkers with high sensitivity and specificity. Further described are compositions and methods for laboratory, kit, field test, smart test, and point-of-care tests for measuring biomarkers in a sample from a subject. Astonishingly, such high accuracy is not affected by any others diseases in the subject, furthermore indicating high sensitivity and specificity of these biomarkers in identifying mTBI as well as moderate and severe traumatic brain injury.

Prior to any brain injury or suspected brain injury, or traumatic mechanism of injury but without TBI, normal and healthy saliva samples were collected from each subject at different points of time such as within one hour, after one to six hours of exercise, at two, three, seven days and fourteen days. Ten minutes prior to the collection of unstimulated saliva samples, subjects were asked to rinse orally with water. At the time of sample collection, subjects were asked to relax for 5-15 minutes. They were then seated in a bent forward position in an ordinary chair and asked to put their tongues on the lingual surfaces of the upper incisors and allow the saliva to drip into sterile plastic (glass) tubes treated with 50 g of 2% sodium azide solution to prevent microbial decomposition of saliva. The tubes were held to the lower lip for 10 minutes resulting in a collection of 1-5 ml of saliva per individual. Saliva samples were then centrifuged using a Sorvall RT6000D centrifuge (Sorvall, Minn.) at 1800 rpm for 5 minutes to remove debris and were immediately frozen at −80° C. awaiting further analysis.

The compositions and methods described herein detail the invention of a process for detection of a novel combination of salivary biomarkers and biomarker complexes which allow for detection, screening or diagnosis of concussion (mTBI) as well as moderate and severe traumatic brain injury. Production of these proteins NSE, GFAP, UCH-L1, IL-1β, IFN-γ, IL-8, IL-10, Spectrin II, and/or 8-OHdG is changed in response to mTBI and more severe TBI. These changes lead to changes in salivary levels of these proteins, which are detectable using a variety of different assays, methods, and other analysis systems.

The biomarkers used herein to predict, diagnose, detect, treat or monitor mTBI and more severe forms of TBI may be measured using any process known to those with skill in the art including, but not limited to, enzyme linked fluorescence polarization immunoassay (FPIA), homogeneous immunoassays, point-of-care tests using conventional lateral flow immunochromatography (LFA), quantitative point-of-care tests using determination of chemiluminescence, fluorescence, and magnetic particles, latex agglutination, biosensors, gel electrophoresis, gas chromatograph-mass spectrometry (GC-MS), nanotechnology, immunoassay, separation immunoassays, heterogeneous immunoassays, homogenous immunoassays, paper-based microfluidic devices (Yetisen A K, Akram M S, Lowe C R, Paper-based Microfluidic Point-Of-Care Diagnostic Devices. Lab Chip. 2013; 13(12): 2210-51), enzyme-linked immunosorbent assay (ELISA), indirect ELISA, sandwich ELISA (Tahara T, Usuki K, Sato H, Ohashi H, Morita H, Tsumura H, Matsumoto A, Miyazaki H, Urabe A, Kato T, A Sensitive Sandwich ELISA for Measuring Thrombopoietin in Human Serum: Serum Thrombopoietin Levels in Healthy Volunteers and in Patients with Haemopoietic Disorders. Br. J. Haematol. 1996; 93(4): 783-8.), competitive ELISA (European patent application EP0202890 A2), multiple ELISA, western blotting, protein immunoblot, mass spectrometry (MS), electrospray ionization (ESI), matrix-assisted laser desorption/ionization (MALDI), protein microarray, protein chip, multiplex detection assay, DNA microarray, SAGE, multiplex PCR, multiplex ligation-dependent probe amplification, LUMINEX®/XMAP®, aptamer-based assay, SOMASCAN® assay, LUMINEX®-based immunoassay, enzyme immunoassays, radioimmunoassays, chemiluminescent assays, microfluidic or MEMS technologies, re-engineering technologies (e.g., instruments utilizing sensors for biomarkers used for telemedicine purposes), epitope-based technologies, other fluorescence technologies, microarrays, lab-on-a-chip, and rapid point-of-care, and biomarker-based mouth guard appliance screening techniques. These technologies include qualitative or quantitative measurement of the levels of biomarkers for mTBI and moderate and severe traumatic brain injury in a biological sample such as saliva. For example and as shown in Example 1 below, biomarkers may be identified using an ELISA test specific for the biomarker(s) of interest. All of the foregoing may be characterized as types of measurement devices operable to provide a qualitative or quantitative level of a measurable label for one or more biomarkers in the saliva sample indicative that the subject has mTBI.

A biomarker based mouth guard appliance consists of a wireless amperometric circuit or other circuit system, paired with a bluetooth low-energy communication system-on-chip which is fully integrated with salivary biomarkers, an integrated biosensor, or other assays for continuous and real-time biomarker monitoring. The sensor or assay is made from different materials such as paper, plastic foil, etc. and is designed to be integrated into an ordinary mouth guard. It is also possible to send this information to a connected smartphone, or computer, or any monitoring system in close to real time.

At least one of the biomarkers is an important target for therapeutic intervention in mTBI and moderate and severe traumatic brain injury. The approach described herein is completely different from the conventional approach of identifying salivary biomarkers for mTBI and more severe forms of traumatic brain injury, which focuses on nervous system proteins released by damaged or traumatically-injured brain cells.

The compositions and methods described herein constitute a combination of biomarkers, which includes, but is not limited to, the following proteins: NSE, GFAP, UCH-L1, IL-1β, IFN-γ, IL-8, IL-10, Spectrin II, and/or 8-OHdG and any combination thereof. The panel of these biomarkers distinguishes mTBI patients from normal healthy subjects. Salivary levels of at least two biomarkers are changed beyond the cutoff values in 70 to 96% of mTBI patients, while 0 to 5% of healthy controls have changes in salivary levels of two biomarkers.

The compositions and methods described herein also constitute combinations of the aforesaid biomarkers. For example, the combination of the biomarkers UCH-L1 and IL-8 have been unexpectedly found to be highly predictive of mTBI in the broadest possible age range of subjects from children through older populations within just a few minutes after the suspected mTBI event through fourteen days or longer after the suspected mTBI event. It is theoretically expected that the combinations would be efficacious in determining mTBI in children as young as six (6) years of age through senior citizens aged 90 or greater. Furthermore, the combination of the aforementioned biomarkers UCH-L1 and GFAP and the combination of UCH-L1 and NSE have been unexpectedly found to be highly predictive of mTBI in the broadest possible age range of subjects from children through older people within minutes after the suspected mTBI event through fourteen days or longer after the suspected mTBI injury. It is again theoretically expected that these two biomarker combinations would be efficacious in determining mTBI in children as young as six (6) years of age through senior citizens aged 90 or greater.

Therefore, provided herein is a method for identifying concussion or traumatic brain injury such as mTBI, as well as moderate to severe TBI. The method comprises the steps of taking a test sample from a subject, where the sample includes a bodily fluid, especially saliva; completing a reaction in vitro by contacting the test sample with a binding agent. A binding agent specifically binds to one or more biomarker. One binding agent or more than one binding agent (e.g., a combination of separate or mixed binding agents) may be implemented. An example of a specific binding agent for detecting salivary biomarkers or the one or more biomarkers is an antibody such as a monoclonal antibody or a polyclonal antibody, etc. capable of binding to the biomarker being detected. Preferably, an antibody is conjugated with a detectable label to form a complex that can be detected. The change in the level of the complex, including NSE, GFAP, UCH-L1, IL-1β, IFN-γ, IL-8, IL-10, Spectrin II, and/or 8-OHdG compared to a healthy control, is useful to indicate mild concussion (mTBI), or moderate TBI, or severe traumatic brain injury (TBI). One, or two, or more than two of the biomarkers described herein (NSE, GFAP, UCH-L1, IL-1β, IFN-γ, IL-8, IL-10, Spectrin II, and/or 8-OHdG) also indicate clinical targets. For example, inhibition of any one or two of the biomarkers leads to clinical improvement of a subject having been diagnosed with mild concussion (mTBI), or moderate TBI, or severe traumatic brain injury (TBI).

The term "therapeutically effective dosage", as used herein, refers to an amount of a pharmaceutical agent to treat or improve an identified disease or condition, or to show a detectable therapeutic or inhibitory effect, such as mitigation or amelioration of symptoms. The effect can be detected or estimated by known methods of the art. The invention here also provides a method of treating, mTBI, as well as moderate to severe TBI, by administering an inhibitor of any of the biomarkers: NSE, GFAP, UCH-L1, IL-1β, IFN-γ, IL-8, IL-10, Spectrin II, and/or 8-OHdG. Those skilled in the art will realize that it is occasionally necessary to make routine variations to the dosage depending on age, route of administration, and condition of the patient such as age, weight, and clinical condition of the recipient patient.

EXAMPLES

The following studies and the examples and data are provided to illustrate the invention, but are not intended to limit the scope of the invention in any way.

Example 1

Example 1 was conducted to determine the levels of NSE, GFAP, UCH-L1, IL-1β, IFN-γ, IL-8, IL-10, Spectrin II, and/or 8-OHdG in test subjects over time after sport-related concussion (SRC) as compared with two non-concussed control groups. Example 1 was 20 further conducted to determine whether these biomarkers existent after sport-related concussion (SRC) could be useful to determine the time in which a person suspected have of having brain injury could return to play (RTP) or, in other words, could safely return to playing of the sport.

The study of Example 1 was performed as follows. Two hundred fifty-six (256) Joint National College Athletic Association (JNCA) Division I and II collegiate contact sport athletes were initially selected for the study. Informed and written consents were obtained from each participant. Matched sex and age of athletes with sport-related concussion (SRC) and athlete controls (AC) were selected. Forty (40) subjects were enrolled as SRC subjects, from a pool of two hundred fifty-six (256) contact sport athletes (178 subjects were excluded due to inclusive diagnosis), and underwent saliva sampling, as described below, and cognitive testing prior to the sports season, and were followed prospectively for a diagnosis of SRC. Athlete control subjects (AC) underwent saliva sampling at the same time points (i.e., baseline within one hour, after 1-6 hours of exercise, at 2, 3, and 7 days) as SRC subjects. The athlete subjects were followed prospectively for a diagnosis of SRC during the season. SRC was defined as an injury witnessed by an on-field certified athletic trainer and meeting the definition of concussion as defined by the Sport Concussion Assessment Tool 2 (McCrory P, Meeuwisse W, Johnston K, et al., Consensus Statement on Concussion in Sport: the 3rd International Conference on Concussion in Sport Held in Zurich. November 2008. J. Athletic Train. 2009; 44:434-448.) This tool gives a structured framework for evaluating 22 post-concussive symptoms including orientation, memory, recall, balance, and gait. In athletes with a diagnosed SRC, plasma samples were obtained within six hours of injury, and then at two, three, and seven days post injury. Saliva sampling was also performed in two control groups; non-concussed athlete controls (AC) had saliva taken at the same time points as the SRC athletes and healthy, non-athlete controls (NAC) at an unrelated time point.

Athletes and controls had repeat testing using Balance Error Scoring System (BESS) and Immediate Post-Concussion Assessment and Cognitive Testing (ImPACT) seven days following the date of the concussion. Healthy non-athlete control subjects (NACs) were recruited through a protocol to obtain saliva samples from participants without a history of head injuries. Head injury history was determined by the Ohio State Traumatic Brain Injury Identification Method, which is both suitable and consistent in detecting lifetime histories of traumatic brain injuries (TBIs) (Corrigan J D, Bogner J, Initial Reliability and Validity of the Ohio State University TBI Identification Method. J. Head Trauma Rehabil. 2007; 22:318-329.) Controls were selected from a pool of participants and matched to SRC athletes in sex and age.

RTP for each athlete was determined by the athletic trainers or team physicians at their respective universities. Both universities followed the NCAA RTP guidelines, which recommend that athletes be asymptomatic at rest and with each step of the RTP progression before returning to their sport. (http://www.ncaa.org/sport-science-institute/concussion-diagnosis-and-management-best-practices.)

Clinical outcome after SRC was determined by changes in cognitive performance, post-concussive symptoms, and postural stability from baseline to seven days following a SRC. Determination of cognition and postural stability was made using ImPACT and BESS, respectively. ImPACT is a proprietary computer program that measures verbal memory, visual memory, reaction time, and visuomotor speed (Collins M W, Iverson G L, Lovell M R, McKeag D B, Norwig J, Maroon J, On-Field Predictors of Neuropsychological and Symptom Deficit Following Sports-Related Concussion. Clin. J. Sport Med 2003; 13:222-229), and a post-concussive symptom inventory (Iverson G L, Lovell M R, Collins M W, Interpreting Change on ImPACT Following Sport Concussion. Clin. Neuropsychologist 2003; 17:460-467.) Athletes were instructed to complete the ImPACT test on a desktop computer in a quiet room.

Each BESS assessment consisted of three stances (double, single, and tandem) in two conditions (firm surface and foam surface), all performed with the eyes closed for 20 seconds per stance. A trained member of the study staff followed the standard procedures for BESS administration. The BESS score is calculated by adding one error point for each performance error, with a maximum of ten errors per stance. (McCrea M, Hammeke T, Olsen G, Leo P, Guskiewicz K, Unreported Concussion in High School Football Players: Implications for Prevention. Clin. J. Sport Med 2004; 14:13-17.) Saliva samples were obtained within one hour of injury, within six hours, after two days, four days, one week and two weeks after injury.

Saliva samples were collected from each subject, including the subjects in the sport-related concussion group (SRC) and in the non-athlete (NAC) and athlete (AC) control groups. Ten to fifteen minutes prior to collection of unstimulated saliva samples, subjects were asked to rinse orally with water. At the time of sample collection, each subject was asked to relax for 5-15 minutes. They were then seated in a bent forward position in an ordinary chair and asked to put their tongues on the lingual surfaces of the upper incisors and to allow the saliva to drip into sterile plastic (glass) tubes treated with 50 g of 2% sodium azide solution, to prevent microbial decomposition of saliva. The tubes were held to the lower lip for 10 minutes resulting in a collection of 1-5 ml of saliva per individual. Saliva samples were then centrifuged using a Sorvall RT6000D centrifuge (Sorvall, Minn.) at 1800 rpm for 5 minutes to remove debris and were then immediately frozen at −80° C., awaiting further analysis.

The following analyses of the biomarkers in the saliva samples were performed for each SRC, AC, and NAC subject using various measurement devices: salivary NSE was analyzed by using a Modular E170 instrument; Roche Diagnostics, Mannheim, Germany with reagents from the same manufacturer; GFAP was analyzed with an enzyme-linked immunosorbent assay (ELISA) via a commercial kit according to the manufacturer's protocol, Biovendor, Candler, NC, USA; UCH-L1 was analyzed using sandwich ELISA; IL-1β was analyzed using chemiluminescent enzyme linked immunoassay from Immulite, Siemens, Germany; IFN-γ was analyzed with an enzyme-linked immunosorbent assay kit from eBioscience, San Diego, USA; IL-8 was analyzed using a commercial ELISA kit from Thermofisher Scientific; IL-10 was analyzed using an ELISA kits R&D System; Spectrin II was analyzed using a commercial ELISA kit from Thermofisher Scientific; and 8-OHdG was analyzed using ELISA Kit (BioVision, USA).

Salivary biomarker concentrations were compared among the three groups using an ANOVA, with a Bonferroni post hoc test at all 6 time points. Area under the curve (AUC) using a receiver operating characteristic analysis was also used to determine the screening ability of salivary biomarkers at each time point to predict group, that is, the area under the receiver operating characteristic curve (AUC) was calculated for determining the prognostic accuracy of the salivary biomarkers.

Data were analyzed by using Statistical Package for the Social Sciences (SPSS version 22; IBM Corporation, Armonk, NY.)

Results: As indicated in Table 1, both the Athlete Controls (AC) and non-athletic controls (NAC), as well as the athletes with SRC, had similar demographic variables.

As indicated in Table 2, the sport-related concussion athlete group (SRC) had significant changes in NSE, GFAP, UCH-L1, IL-1β, IFN-γ, IL-8, IL-10, Spectrin II, and 8-OHdG levels when compared to non-athlete controls (NAC) ($p=0.005$, Table 2) and non-concussed athlete controls (AC) at baseline, as well as at all other time points.

The SRC group had significant changes of NSE, GFAP, UCH-L1, IL-1β, IFN-γ, IL-8, IL-10, Spectrin II, and 8-OHdG compared to AC and NAC, at all time points ($p=0.005$, Table 2). The data of Table 2 indicate that the biomarkers NSE, GFAP, UCH-L1, IL-1β, IFN-γ, IL-8, IL-10, Spectrin II, and 8-OHdG are useful to identify the existence of brain injury including mTBI in the test subjects.

TABLE 1

Characteristics of Study Participants

| Characteristics | NAC (n = 40) | AC (n = 38) | SRC (n = 40) | |
|---|---|---|---|---|
| Gender M:F | 20:20 | 20:18 | 20:20 | P = 0.76 |
| Age in years Mean (SD) | 19.2 (1.3) | 19.1 (1.2) | 19.2 (1.4) | P = 0.68 |

TABLE 2

Salivary Biomarker Comparison in Sport-Related Concussion Subjects (SRC), Athlete Control Subjects (AC), and Healthy Non-Athlete Control Subjects (NAC)

| | Timing | NSE (pg/ml) | GFAP (pg/ml) | UCH-L1 (pg/ml) | IL-1β (pg/ml) | IFN-γ (pg/ml) | IL-8 (pg/ml) | IL-10 (pg/ml) | Spectrin II (ng/ml) | 8-OHdG (ng/ml) |
|---|---|---|---|---|---|---|---|---|---|---|
| NAC | Within 1 hour or 30(15) mins | 0.1 (0.2) | 0.1 (0.1) | 9.5 (1.5) | 142 (35) | 8.1 (0.9) | 276 (55) | 1.5 (0.6) | 0.9 (0.7) | 0.89 (0.64) |
| | 1-6 hours | 0.2 (0.5) | 0.5 (0.6) | 9.7 (1.3) | 143 (24) | 8.09 (0.96) | 278 (45) | 1.5 (0.7) | 0.9 (0.6) | 1.01 (0.62) |
| | 2 Days | 0.1 (0.2) | 0.6 (0.7) | 9.6 (1.3) | 145 (35) | 8 (0.3) | 277 (52) | 1.4 (0.8) | 1.9 (0.9) | 0.87 (0.67) |
| | 3 Days | 0.1 (0.1) | 0.5 (0.4) | 9.4 (1.4) | 143 (36) | 8.1 (0.07) | 275 (63) | 1.5 (1.2) | 1.6 (1.2) | 0.86 (0.48) |
| | 7 Days | 0.1 (0.04) | 0.6 (0.5) | 9.3 (1.3) | 142 (41) | 8.04 (0.05) | 276 (58) | 1.4 (0.9) | 1.5 (0.6) | 0.84 (0.52) |
| | 14 Days | 0.1 (0.03) | 0.5 (0.4) | 9.2 (1.8) | 140 (53) | 8.1 (0.08) | 278 (61) | 1.5 (0.8) | 1.7 (1.1) | 0.83 (0.45) |
| AC | Within 1 hour | 0.2 (0.3) | 0.7 (0.1) | 9.9 (3.2) | 123 (45) | 9.12 (2.78) | 256 (65) | 1.3 (0.7) | 1.8 (0.7) | 1.01 (0.43) |
| | 1-6 hours | 0.3 (0.4) | 0.8 (0.3) | 9.8 (2.8) | 146 (32) | 10.01 (0.84) | 301 (62) | 2.0 (0.9) | 2.3 (0.9) | 1.09 (0.65) |
| | 2 Days | 0.1 (0.2) | 0.6 (0.5) | 9.3 (2.3) | 134 (63) | 8.56 (1.56) | 287 (68) | 1.5 (1.1) | 2.1 (0.7) | 0.87 (0.46) |
| | 3 Days | 0.2 (0.3) | 0.4 (0.3) | 9.4 (3.1) | 145 (46) | 7.89 (1.34) | 276 (71) | 1.4 (0.8) | 1.9 (0.8) | 0.84 (0.57) |
| | 7 Days | 0.2 (0.1) | 0.5 (0.2) | 9.2 (2.3) | 144 (53) | 7.92 (1.78) | 299 (68) | 1.6 (1.1) | 1.6 (1.2) | 0.85 (0.32) |
| | 14 Days | 0.1 (0.1) | 0.4 (0.2) | 9.4 (3.1) | 136 (49) | 7.45 (2.09) | 208 (70) | 1.7 (0.9) | 1.5 (0.9) | 0.83 (0.41) |
| SRC | Within 1 hour | 1.6 (0.3) | 1.543 (0.314) | 12.9 (7.5) | 278 (48) | 19.5 (0.68) | 567 (117) | 4.8 (0.6) | 12.7 (2.3) | 3.46 (1.31) |
| | 1-6 hours | 1.8 (0.5) | 1.923 (0.212) | 54.6 (8.4) | 308 (46) | 20.8 (0.72) | 709 (104) | 5.9 (0.8) | 13.2 (1.2) | 4.08 (0.78) |
| | 2 Days | 1.7 (0.4) | 1.845 (0.207) | 13.4 (5.2) | 314 (53) | 22.4 (0.65) | 817 (158) | 5.7 (0.5) | 12.8 (1.4) | 3.56 (1.27) |
| | 3 Days | 1.5 (0.3) | 1.782 (0.254) | 12.9 (2.7) | 354 (42) | 23.7 (0.83) | 784 (136) | 5.5 (0.7) | 11.5 (2.4) | 3.24 (1.31) |
| | 7 Days | 1.4 (0.4) | 1.509 (0.546) | 12.4 (3.3) | 284 (62) | 20.5 (0.67) | 675 (148) | 5.3 (0.4) | 12.3 (1.6) | 3.36 (1.26) |
| | 14 Days | 1.3 (0.5) | 1.478 (0.732) | 11.5 (2.8) | 274 (63) | 19.4 (0.58) | 672 (127) | 5.4 (0.5) | 11.4 (1.3) | 3.24 (1.47) |

The biomarkers IL-8 and UCH-L1 were evaluated separately and in combination to evaluate the capability of these biomarkers to identify mTBI in the control and SRC subjects. The data are presented in Table 3. Elevated levels of IL-8 and UCH-L1 showed a significant correlation with the existence of mTBI and served to differentiate between the control subjects and the subjects suspected of having sustained mTBI.

TABLE 3

Area Under the Curve for Distinguishing Between mTBI and Controls Utilizing IL-8 and UCH-L1 Biomarkers

| Time Post-Injury | IL-8 | UCH-L1 | Combination of IL-8 and UCH-L1 |
|---|---|---|---|
| Within one hour | 0.85 (0.81-0.98) | 0.89 (0.83-1.00) | 0.92 (0.85-1.00) |
| 1-6 hours | 0.89 (0.72-0.95) | 0.89 (0.75-1.00) | 0.93 (0.84-1.00) |
| 2 days | 0.78 (0.65-0.94) | 0.80 (0.76-1.00) | 0.90 (0.82-0.94) |
| 4 days | 0.70 (0.65-0.90) | 0.78 (0.71-0.95) | 0.85 (0.68-0.97) |
| 1 week | 0.72 (0.64-0.94) | 0.80 (0.70-1.00) | 0.89 (0.76-1.00) |
| 2 weeks | 0.70 (0.64-0.90) | 0.78 (0.70-0.95) | 0.85 (0.78-1.00) |

As was previously illustrated in Table 2, salivary NSE, GFAP, UCH-L1, IL-1β, IFN-γ, IL-8, IL-10, Spectrin II, and 8-OHdG concentrations within one hour of the suspected brain injury, and at 1-6 hours, 2 days, 4 days, 1 week, and 2 weeks following the suspected brain injury could differentiate sport-related concussion (SRC) subjects from the control subjects, both athlete control (AC) and non-athlete control (NAC), with an AUC (0.83-0.92, p=0.0050). Furthermore and as illustrated in Table 3, IL-8 and UCH-L1 concentrations within 1 hour and 1-6 hours after the suspected injury in the SRC subjects were increased in players with good screening utility for mTBI (AUC 0.85, 0.89 and 0.89, 0.89, p=0.005 respectively for the IL-8 and UCH-L1, Table 3)

As illustrated in the following Table 4, the specificity and sensitivity of both biomarkers IL-8 and UCH-L1 in predicting mTBI was very high. In Table 4, NPV refers to negative predictive value while PPV refers to positive predictive value.

TABLE 4

Predictive Value of Salivary UCH-L1 and IL-8 Levels for mTBI

| Biomarker | Cutoff | Sensitivity | Specificity | PPV | NPV |
|---|---|---|---|---|---|
| UCH-L1 | 11 pg/ml | 79 | 0.93 | 0.81 | 0.76 |
| IL-8 | 500 pg/ml | 75 | 0.86 | 0.73 | 0.70 |

The biomarkers UCH-L1 and NSE were evaluated separately and in combination to evaluate the capability of these biomarkers to identify mTBI in the control and SRC subjects. The data are presented in Table 5. Elevated levels of UCH-L1 and NSE showed a significant correlation with the existence of mTBI and served to differentiate between the control subjects and the subjects suspected of having sustained mTBI.

TABLE 5

Area Under the Curve for Distinguishing Between mTBI and Controls Utilizing UCH-L1 and NSE Biomarkers

| Time Post-Injury | NSE | UCH-L1 | Combination of UCH-L1 and NSE |
|---|---|---|---|
| Within one hour | 0.72 (0.65-0.89) | 0.89 (0.83-1.00) | 0.89 (0.81-1.00) |
| 1-6 hours | 0.80 (0.70-0.96) | 0.89 (0.75-1.00) | 0.90 (0.86-1.00) |
| 2 days | 0.75 (0.62-0.93) | 0.80 (0.76-1.00) | 0.86 (0.80-0.93) |
| 4 days | 0.68 (0.63-0.92) | 0.78 (0.71-0.95) | 0.83 (0.62-1.00) |
| 1 week | 0.65 (0.58-0.92) | 0.80 (0.70-1.00) | 0.82 (0.74-1.00) |
| 2 weeks | 0.64 (0.57-0.86) | 0.78 (0.70-0.95) | 0.81 (0.76-1.00) |

As illustrated in Table 5, UCH-L1 and NSE concentrations within 1 hour and 1-6 hours after the suspected injury in the SRC subjects were increased in players with good screening utility for mTBI (AUC 0.72; 0.89 and 0.80, 0.89, p=0.005 respectively, Table 5).

As illustrated in the following Table 6, the specificity and sensitivity of both biomarkers UCH-L1 and NSE in predicting mTBI was very high. In Table 6, NPV once again refers to negative predictive value while PPV once again refers to positive predictive value.

TABLE 6

Predictive Value of Salivary UCH-L1 and NSE Levels for mTBI

| Biomarker | Cutoff | Sensitivity | Specificity | PPPV | NNPV |
|---|---|---|---|---|---|
| UCH-L1 | 11 pg/ml | 79 | 0.93 | 0.81 | 0.76 |
| NSE | 0.09 pg/ml | 73 | 0.78 | 0.71 | 0.68 |

The biomarkers UCH-L1 and GFAP were evaluated separately and in combination to evaluate the capability of these biomarkers to identify mTBI in the control and SRC subjects. The data are presented in Table 7. Elevated levels of UCH-L1 and GFAP showed a significant correlation with the existence of mTBI and served to differentiate between the control subjects and the subjects suspected of having sustained mTBI.

TABLE 7

Area Under the Curve for Distinguishing Between mTBI and Controls Utilizing UCH-L1 and GFAP Biomarkers

| Time Post-Injury | GFAP | UCH-L1 | Combination of UCH-L1 and GFAP |
|---|---|---|---|
| Within one hour | 0.70 (0.62-0.90) | 0.89 (0.83-1.00) | 0.89 (0.82-1.00) |
| 1-6 hours | 0.74 (0.68-0.89) | 0.89 (0.75-1.00) | 0.90 (0.85-1.00) |
| 2 days | 0.72 (0.60-0.94) | 0.80 (0.76-1.00) | 0.83 (0.78-0.91) |
| 4 days | 0.66 (0.61-0.94) | 0.78 (0.71-0.95) | 0.81 (0.60-1.00) |
| 1 week | 0.63 (0.54-0.89) | 0.80 (0.70-1.00) | 0.81 (0.74-0.98) |
| 2 weeks | 0.62 (0.56-0.88) | 0.78 (0.70-0.95) | 0.81 (0.74-0.96) |

As illustrated in Table 7, UCH-L1 and GFAP concentrations within 1 hour and 1-6 hours after the suspected injury in the SRC subjects were increased in players with good screening utility for mTBI (AUC 0.70; 0.89 and 0.74, 0.89, p=0.005 respectively, Table 7).

As illustrated in the following Table 8, the specificity and sensitivity of both biomarkers UCH-L1 and GFAP in predicting mTBI was very high. In Table 8, NPV once again refers to negative predictive value while PPV once again refers to positive predictive value.

TABLE 8

Predictive Value of Salivary UCH-L1 and GFAP Levels for mTBI

| Variable | Cutoff | Sensitivity | Specificity | PPPV | NNPV |
|---|---|---|---|---|---|
| UCH-L1 | 11 pg/ml | 79 | 0.93 | 0.81 | 0.76 |
| GFAP | 1.0 pg/ml | 72 | 0.72 | 0.72 | 0.67 |

Within the sport-related concussion (SRC) group of subjects, there were no differences in sport played, or history of concussion, based on long RTP (number of subjects=17; >15 days) vs short RTP (number of subjects=23; Less than 15 days). Higher levels of salivary NSE and GFAP, UCH-L1 and IL-8 measured within 6 hours of SRC significantly relates to increasing the time period within which the athlete is permitted to return to play (RTP).

Table 9 below illustrates significant observed differences in salivary NSE and GFAP, UCH-L1 and IL-8 levels in long RTP and short RTP (Table 9, p=0.005), indicating that salivary NSE and GFAP, UCH-L1, and IL-8 in diagnosis, screening, monitoring, early detection, prognosis, differentiate long RTP from short RTP.

TABLE 9

Different Salivary Biomarker Levels in Long RTP and Short RTP

| | Timing | NSE (pg/ml) | GFAP (pg/ml) | UCH-L1 (pg/ml) | IL-1β (pg/ml) | IFN-γ (pg/ml) | IL-8 (pg/ml) | IL-10 (pg/ml) | Spectrin II (ng/ml) | 8-OHdG (ng/ml) |
|---|---|---|---|---|---|---|---|---|---|---|
| Within 1 hour | Long RTP | 1.9 (0.2) | 1.872 (0.309) | 15.4 (2.6) | 302 (52) | 22.5 (1.09) | 624 (116) | 5.3 (0.9) | 13.8 (2.5) | 3.57 (1.64) |
| | Short RTP | 1.2 (0.4) | 11.454 (0.308) | 11.9 (1.7) | 216 (42) | 16.7 (0.73) | 524 (109) | 4.4 (0.5) | 12.8 (2.1) | 3.23 (1.28) |
| 1-6 hours | Long RTP | 2.3 (0.5) | 2.653 (00.404) | 67.4 (6.8) | 334 (51) | 23.6 (0.42) | 813 (103) | 6.1 (0.9) | 13.8 (1.5) | 4.13 (0.99) |
| | Short RTP | 1.7 (0.6) | 1.765 (0.423) | 42.5 (7.7) | 216 (62) | 18.5 (.67) | 623 (104) | 5.4 (0.6) | 12.6 (1.6) | 3.97 (0.83) |
| 2 Days | Long RTP | 1.8 (0.2) | 2.163 (0.398) (0.207) | 15.6 (1.5) | 322 (41) | 24.7 (0.57) | 846 (137) | 5.9 (0.6) | 13.7 (1.3) | 3.72 (1.05) |
| | Short RTP | 1.4 (0.5) | 1.542 (0.364) | 12.5 (3.6) | 301 (58) | 21.6 (1.36) | 568 (166) | 5.5 (0.8) | 11.9 (1.6) | 3.25 (1.32) |

TABLE 9-continued

Different Salivary Biomarker Levels in Long RTP and Short RTP

| | Timing | NSE (pg/ml) | GFAP (pg/ml) | UCH-L1 (pg/ml) | IL-1β (pg/ml) | IFN-γ (pg/ml) | IL-8 (pg/ml) | IL-10 (pg/ml) | Spectrin II (ng/ml) | 8-OHdG (ng/ml) |
|---|---|---|---|---|---|---|---|---|---|---|
| 3 | Long | 1.7 | 1.914 | 15.6 | 366 | 24.6 | 807 | 5.7 | 12.3 | 3.37 |
| Days | RTP | (0.3) | (0.215) | (1.5) | (42) | (0.94) | (107) | (0.8) | (11.4) | (1.43) |
| | Short | 1.1 | 1.365 | 10.64 | 324 | 21.8 | 518 | 5.2 | 10.8 | 3.19 |
| | RTP | (0.2) | (0.312) | (1.9) | (67) | (0.68) | (114) | (0.6) | (3.3) | (1.54) |
| 7 | Long | 1.5 | 1.667 | 14.7 | 290 | 21.2 | 703 | 5.4 | 12.9 | 3.64 |
| Days | RTP | (0.6) | (0.483) | (1.4) | (60) | (0.6/) | (114) | (0.6) | (6.8) | (1.78) |
| | Short | 1.1 | 1.124 | 10.32 | 280 | 19.8 | 498 | 5.2 | 11.1 | 3.21 |
| | RTP | (0.5) | (0.267) | (1.5) | (56) | (0.88) | (109) | (0.4) | (2.1) | (1.82) |
| 14 | Long | 1.9 | 1.655 | 13.6 | 280 | 20.8 | 698 | 5.5 | 12.0 | 3.64 |
| Days | RTP | (0.4) | (0.652) | (2.1) | (64) | (0.62) | (103) | (0.7) | (1.7) | (1.48) |
| | Short | 1.1 | 1.102 | 10.3 | 265 | 18.6 | 402 | 5.4 | 11.2 | 3.15 |
| | RTP | (0.6) | (0.321) | (3.3) | (75) | (0.66) | (154) | (0.6) | (1.5) | (1.25) |

Example 2

Example 2 was conducted to determine a time course and diagnostic accuracy of salivary biomarkers in a cohort of trauma patients with mild traumatic brain injury (mTBI.)

The study of Example 2 was performed as follows. Informed and written consents were taken from each participant. Eligibility for mTBI was estimated by the treating sport physician and neurologist based on the subject having a history of blunt head trauma followed by symptoms of either loss of consciousness, amnesia, or disorientation within three hours of injury and the subject having a GCS score of 9 to 15. Head CT scans were performed on the subject at the discretion of the treating physician and neurologist. Potential subjects were excluded on the basis of the following criterion: the subject was less than 18 years of age, the subject had not had a trauma event, the subject was known to have had dementia, CNS problems and chronic psychosis, the subject was pregnant, and the subject had low blood pressure.

The non-TBI general trauma group included patients with a GCS score of 15 examined with a traumatic mechanism of injury but without TBI. These subjects had experienced similar mechanisms of injury as the mTBI group, but all had a good mental status without any evidence of acute brain injury or hemodynamic unsteadiness. These patients were carefully screened to make sure that they had no loss of consciousness, no amnesia, and no alteration in sensory at any time after injury.

Saliva samples were taken within 20-60 minutes after injury, and four, eight, twelve, sixteen, twenty four, and forty eight hours after injury from each subject. A CT scan of the head from trauma patients was taken under physician direction. The diagnostic values of salivary NSE, GFAP, UCH-L1, IL-1β, IFN-γ, IL-8, IL-10, Spectrin II, and 8-OHdG in detecting brain injury were evaluated. The outcomes observed included the performance of the biomarkers for (1) detecting the presence of mTBI and distinguishing trauma patients with mTBI from those without mTBI, and (2) identifying traumatic intracranial lesions by means of a CT scan to confirm the indications of mTBI provided by the biomarkers. As is known, a CT scan is capable of detecting intracranial lesions such as intracranial hemorrhage, contusion, diffuse axonal injury, cerebral edema, pneumocephalus, and midline shift of intracranial contents and the CT scan data was taken to confirm the biomarker results.

The Spearman rank correlation coefficient (ρ) was used for analyses of correlation between biomarkers and age. The AUC is the most commonly used measure for diagnostic accuracy of quantitative tests, namely, best to classify patients in two groups such as those with and those without the outcome of interest. Confidence intervals (CI) consist of a range of possible values of the unknown population parameter. (Neyman, J, Outline of a Theory of Statistical Estimation Based on the Classical Theory of Probability. Philosophical Transactions of the Royal Society A. 236 (767): 333-380 1937.)

Data were analyzed by using a Statistical Package for the Social Sciences (SPSS version 22; IBM Corporation, Armonk, NY.)

Members of a group of 508 trauma patients were examined for participation in the study with 208 subjects being selected in accordance with the inclusion and exclusion criteria described above. Of the 208 selected subjects, 102 subjects were suspected to have brain injury and were assigned to the mTBI group while 106 were assigned to the non-mTBI group. As in Table 10, there were no significant differences in demographic characteristics of the mTBI and the non-mTBI groups. Of course and as reflected in Table 10, the mTBI group included members with loss of consciousness and amnesia not found among the non-mTBI group. This is expected because the non-mTBI subjects were required to be free of loss of consciousness, amnesia, and CT-detected intracranial lesions to be included in the study. There was no association between age and any biomarker concentration in concussed players.

TABLE 10

Characteristics of Study Participants

| | mTBI Group N = 102 | Non-mTBI Group N = 106 | p-Value |
|---|---|---|---|
| Mean Age (SD) | 22.3 (10.5) | 23.2 (9.5) | 0.65 |
| Gender (M:F) | 50:52 | 60:46 | 0.56 |
| Cause of Injury (n) | | | |
| Fell Down | 51 | 42 | 0.84 |
| Motor Vehicle Crash | 31 | 42 | 0.67 |
| Sport | 10 | 16 | 0.74 |
| Other | 20 | 5 | 0.12 |
| Loss of Consciousness (n/%) | 63 | 0 | 0.01 |
| Amnesia (n/%) | 10 | 0 | 0.01 |
| Admitted to Hospital (n/%) | 31 | 32 | 0.43 |
| Intoxicated: drugs or alcohol (n/%) | 1 | 1 | 0.75 |

TABLE 10-continued

| Characteristics of Study Participants | | | |
|---|---|---|---|
| | mTBI Group N = 102 | Non-mTBI Group N = 106 | p-Value |
| Head CT Scan Performed (n/%) | 92 | 93 | 0.68 |
| Intracranial Lesions on CT (n/%) | 10 | 0 | 0.01 |

As illustrated in Table 11, two to ten-fold changes in salivary levels of NSE, GFAP, UCH-L1, IL-1β, IFN-γ, IL-8, IL-10, Spectrin II and 8-OHdG were found in mTBI patients within 20-60 minutes i.e., 30 (15) (values represent mean and standard deviation respectively) minutes when comparing mTBI to non-mTBI samples. Concentrations of NSE, GFAP, UCH-L1, IL-1β, IFN-γ, IL-8, IL-10, Spectrin II, and 8-OHdG were significantly higher in patients with intracranial lesions at enrollment and four, eight, twelve, sixteen, twenty-four, forty-eight hours, and seven days after injury.

A determination of the prognostic accuracy of the biomarkers was undertaken with reference to the area under the characteristic curve (AUC). GFAP established a range of AUCs between 0.71 (95% CI, 0.62-0.80) and 0.93 (95% CI, 0.73-0.98), and UCH-L1 confirmed AUCs between 0.73 (95% CI, 0.69-0.98) and 0.89(95% CI, 0.72-0.98.) NSE established a range of AUCs between 0.78 (95% CI, 0.69-0.92) and 0.92 (95% CI, 0.81-0.95), and IL-1β confirmed AUCs between 0.75 (95% CI, 0.68-0.95) and 0.92(95% CI, 0.75-0.96.) IFN-γ established a range of AUCs between 0.65 (95% CI, 0.59-0.72) and 0.78 (95% CI, 0.68-0.92), and IL-1β confirmed AUCs between 0.74 (95% CI, 0.65-0.90) and 0.85(95% CI, 0.79-0.98.) IL-10 established a range of AUCs between 0.71 (95% CI, 0.67-0.78) and 0.82 (95% CI, 0.77-0.90), and Spectrin II confirmed AUCs between 0.7 (95% CI, 0.62-0.84) and 0.82(95% CI, 0.72-0.95). 8-OHdG confirmed AUCs between 0.75 (95% CI, 0.67-0.88) and 0.88(95% CI, 0.79-0.97).

TABLE 11

Salivary levels of NSE, GFAP, UCH-L1, IL-1β, IFN-γ, IL-8, IL-10, Spectrin II and 8-OHdG in mTBI and non-mTBI Groups Mean (SD)

| | Timing | NSE (pg/ml) | GFAP (pg/ml) | UCH-L1 (pg/ml) | IL-1β (pg/ml) | IFN-γ (pg/ml) | IL-8 (pg/ml) | IL-10 (pg/ml) | Spectrin II (ng/ml) | 8OHdG (ng/ml) |
|---|---|---|---|---|---|---|---|---|---|---|
| mTBI | Within | 1.4 | 1.6 | 15.6 | 302 | 18.2 | 678 | 4.8 | 11.4 | 3.56 |
| | 1 hour | (0.6) | (0.5) | (5.3) | (101) | (2.7) | (104) | (0.9) | (2.6) | (1.31) |
| | 4 Hours | 1.5 | 1.7 | 55.2 | 325 | 19.3 | 709 | 5.3 | 13.2 | 4.02 |
| | | (0.4) | (0.5) | (6.7) | (45) | (3.4) | (134) | (0.8) | (3.5) | (1.03) |
| | 8 Hours | 1.7 | 1.8 | 56.8 | 378 | 21.2 | 721 | 5.8 | 14.4 | 4.56 |
| | | (0.2) | (0.4) | (11.3) | (67) | (4.1) | (123) | (0.5) | (3.4) | (2.13) |
| | 12 Hours | 1.6 | 1.5 | 54.7 | 472 | 19.5 | 708 | 6.3 | 12.5 | 4.13 |
| | | (0.3) | (0.5) | (10.9) | (82) | (3.2) | (146) | (0.7) | (4.7) | (1.35) |
| | 16 Hours | 1.8 | 1.4 | 51.6 | 363 | 20.3 | 678 | 5.3 | 13.9 | 4.09 |
| | | (0.4) | (0.4) | (13.4) | (56) | (4.5) | (121) | (0.8) | (5.2) | (1.24) |
| | 24 Hours | 1.6 | 1.3 | 23.6 | 325 | 21.4 | 789 | 5.1 | 13.4 | 4.14 |
| | | (0.3) | (0.2) | (5.8) | (48) | (6.2) | (142) | (0.6) | (4.8) | (1.45) |
| | 48 Hours | 1.7 | 1.4 | 15.7 | 308 | 20.7 | 765 | 5.5 | 14.1 | 4.03 |
| | | (0.4) | (0.5) | (6.2 | (85) | (5.3) | (126) | (0.7) | (5.2) | (1.13) |
| | 7 Days | 1.5 | 1.3 | 17.4 | 291 | 20.3 | 793 | 5.2 | 14.6 | 3.45 |
| | | (0.4) | (0.2) | (6.8) | (53) | (5.2) | (104) | (0.6) | (2.5) | (1.21) |
| Non- | Within | 0.1 | 0.001 | 6.7 | 134 | 5.1 | 254 | 1.2 | 0.6 | 1.04 |
| mTBI | 1 Hour | (0.3) | (0.001) | (2.3) | (67) | (1.2) | (63) | (0.6) | (0.4) | (0.45) |
| | 4 Hours | 0.1 | 0.02 | 5.8 | 125 | 4.7 | 268 | 1.4 | 0.8 | 1.52 |
| | | (0.2) | (0.01) | (4.2) | (58) | (1.4) | (74) | (0.7) | (0.3) | (0.57) |
| | 8 Hours | 0.2 | 0.05 | 6.4 | 138 | 4.6 | 271 | 1.5 | 0.7 | 1.34 |
| | | (0.1) | (0.03) | (3.3) | (75) | (2.3) | (67) | (0.9) | (0.4) | (0.34) |
| | 12 Hours | 0.1 | 0.02 | 5.6 | 146 | 4.3 | 284 | 1.3 | 0.5 | 1.47 |
| | | (0.4) | (0.03) | (3.6) | (58) | (2.1) | (72) | (0.6) | (0.5) | (0.42) |
| | 16 Hours | 0.2 | 0.03 | 5.3 | 147 | 4.5 | 262 | 1.6 | 0.7 | 1.40 |
| | | (0.2) | (0.03) | (2.2) | (67) | (1.8) | (65) | (0.5) | (0.4) | (0.53) |
| | 24 Hours | 0.3 | 0.02 | 5.2 | 143 | 4.4 | 265 | 1.4 | 0.6 | 1.46 |
| | | (0.2) | (0.01) | (2.4) | (70) | (2.2) | (53) | (0.5) | (0.3) | (0.67) |
| | 48 Hours | 0.1 | 0.1 | 4.8 | 148 | 4.6 | 247 | 1.3 | 0.7 | 1.38 |
| | | (0.2) | (0.3) | (2.6) | (89) | (2.4) | (46) | (0.9) | (0.5) | (0.53) |
| | 7 Days | 0.2 | 0.3 | 6.3 | 153 | 4.4 | 256 | 1.5 | 0.5 | 1.56 |
| | | (0.3) | (0.3) | (4.2) | (92) | (2.1) | (51) | (0.5) | (0.4) | (0.36) |
| P-Value | | <0.001 | <0.001 | <0.001 | <0.001 | <0.001 | <0.001 | <0.001 | <0.001 | <0.001 |

A finding reflected in Table 11 is that levels of UCH-L1 and IL-8 showed the ability to differentiate between the presence of mTBI and non-mTBI. As in the data of Table 12, the combination of UCH-L1 and IL-8, was clearly able to distinguish mTBI from non-mTBI.

The levels of at least two salivary biomarkers were changed above cutoff values in 91% of mTBI patients (Table 11). According to Table 11, elevated levels of the nine biomarkers were observed in the subjects having mild traumatic brain injury (mTBI) as compared with the trauma control subjects.

While comparing mTBI to non mTBI subjects, NSE, GFAP, UCH-L1, IL-1β, IFN-γ, IL-8, IL-10, Spectrin II and 8-OHdG demonstrated a range of AUCs between (0.78-0.93) and (0.65-0.75).

Referring to Table 12, IL-8 and UCH-L1 demonstrated high AUCs at all time points. The specificity and sensitivity in predicting mTBI for both biomarkers IL-8 and UCH-L1 was very high as presented in Table 13. The data of Tables 12-13 show that the combination of UCH-L1 and IL-8 biomarkers are highly efficacious biomarkers for screening, diagnosis, detection, monitoring, or prognosis for mTBI.

TABLE 12

| Area Under the Curve (AUC) for Distinguishing Between mTBI and Non-mTBI | | | |
|---|---|---|---|
| Hours Post Injury | IL-8 | UCH-L1 | Combination of UCH-L1 and IL-8 |
| Within 1 Hour | 0.78 (0.68-0.96) | 0.82 (0.69-0.98) | 0.86 (0.75-1.00) |
| 4 Hours | 0.81 (0.70-0.92) | 0.89 (0.76-0.98) | 0.92 (0.84-1.00) |
| 8 Hours | 0.83 (0.73-0.99) | 0.92 (0.88-1.00) | 0.95 (0.86-1.00) |
| 12 Hours | 0.82 (0.71-0.95) | 0.84 (0.73-0.98) | 0.88 (0.77-1.00) |
| 24 Hours | 0.80 (0.72-0.96) | 0.82 (0.72-0.98) | 0.88 (0.75-1.00) |
| 48 Hours | 0.80 (0.71-0.95) | 0.80 (0.72-0.92) | 0.84 (0.64-1.00) |
| 72 Hours | 0.78 (0.65-0.94) | 0.81 (0.68-0.99) | 0.86 (0.76-0.98) |

TABLE 13

| Positive Predictive Value (PPV) and Negative Predictive Value (NPV) Salivary UCH-L1 and IL-8 levels for mTBI | | | | | |
|---|---|---|---|---|---|
| Biomarker | Cutoff | Sensitivity | Specificity | PPV | NPV |
| UCH-L1 | 11 pg/ml | 81 | 0.94 | 0.82 | 0.78 |
| IL-8 | 500 pg/ml | 73 | 0.83 | 0.72 | 0.70 |

As indicated by Table 14, no correlations were found between age and biomarkers, so the nine biomarkers of Table 14 can be used effectively for screening, diagnosis, detection, monitoring, or prognosis for mTBI.

TABLE 14

| Correlations Between Biomarkers and Age Among all Subjects | | | | | | | | | | |
|---|---|---|---|---|---|---|---|---|---|---|
| | | NSE (pg/ml) | GFAP (pg/ml) | UCH-L1 (pg/ml) | IL-1β (ng/ml) | IFN-γ (pg/ml) | IL-8 (ng/ml) | IL-10 (pg/ml) | Spectrin II (ng/ml) | 8OHdG (ng/ml) |
| mTBI | R | −0.13 | 0.08 | 0.06 | 0.05 | 0.02 | 0.03 | 0.04 | 0.16 | 0.03 |
| non-MTBI and | P value | 0.67 | 0.27 | 0.16 | 0.28 | 0.15 | 0.24 | 0.37 | 0.83 | 0.73 |

The biomarker data indicative of mTBI was confirmatory of the CT scan results. In patients with traumatic intracranial lesions confirmed to exist by the CT scans, NSE, GFAP, UCH-L1, IL-1β, IFN-γ, IL-8, IL-10, Spectrin II and 8-OHdG levels were significantly elevated compared with those without lesions (P<0.001.) Concentrations of UCH-L1, NSE, IL-1β and 8-OHdG were significantly higher in patients with intracranial lesions at enrollment and four, eight, twelve, sixteen, twenty four, and forty eight hours after injury, but not at any later time points. The ability of NSE, GFAP, UCH-L1, IL-1β, IFN-γ, IL-8, IL-10, Spectrin II and 8-OHdG to detect traumatic intracranial lesions detected on CT was assessed over seven days at each time point after injury (Table 11).

Based on the results of Example 2, it can be concluded that salivary NSE, GFAP, UCH-L1, IL-1β, IFN-γ, IL-8, IL-10, Spectrin II, and 8-OHdG act as detection, screening, diagnostic, or treatment biomarkers of mTBI. Salivary biomarkers such as NSE, GFAP, UCH-L1, IL-1β, IFN-γ, IL-8, IL-10, Spectrin II, and 8-OHdG have been identified for the screening, diagnosis and treatment of concussion. Some of these biomarkers, or all of the biomarkers NSE, GFAP, UCH-L1, IL-1β, IFN-γ, IL-8, IL-10, Spectrin II, and 8-OHdG, are targets for therapeutic intervention. Salivary biomarkers described in this invention could easily be measured using a measurement device such as standard ELISA. These salivary biomarkers can be measured by using enzyme linked fluorescence polarization immunoassay (FPIA) and homogeneous immunoassays, point of care tests using conventional lateral flow immunochromatography (LFA), quantitative point of care tests using determination of chemiluminescence, fluorescence, and magnetic particles, latex agglutination, biosensors, gel electrophoresis, gas chromatograph-mass spectrometry (GC-MS), nanotechnology, immunoassay, separation immunoassays, heterogeneous immunoassays, homogenous immunoassays, paper-based microfluidic devices, enzyme-linked immunosorbent assay (ELISA), indirect ELISA, sandwich & competitive ELISA, multiple ELISA, western blotting, protein immunoblot, mass spectrometry (MS), electrospray ionization (ESI), matrix-assisted laser desorption/ionization (MALDI), protein microarray, protein chip, multiplex detection assay, DNA microarray, SAGE, multiplex PCR, multiplex ligation-dependent probe amplification, LUMINEX®/XMAP®, aptamer-based assay, SOMASCAN® assay, LUMINEX®-based immunoassay, enzyme immunoassays, radioimmunoassays, chemiluminescent assays, microfluidic or MEMS technologies, re-engineering technologies (e.g. instruments utilizing sensors for biomarkers used for telemedicine purposes), epitope-based technologies, other fluorescence technologies, microarrays, lab-on-a-chip, and rapid point-of-care screening technologies, and other technologies, i.e., platforms or assays or kits etc. expected to be developed in the future.

Example 3

Example 3 was conducted to analyze the accuracy of a combination biomarker panel of salivary NSE, GFAP, UCH-L1, IL-1β, IFN-γ, IL-8, IL-10, Spectrin II, and 8-OHdG for the diagnosis of, and discrimination between, mTBI and control subjects.

A statistical comparison of the two populations (by the combination of the salivary biomarkers in Examples 1 and 2) was performed using the two-tailed t-test using GraphPad Prism for Windows, v. 5.01 (GraphPad Software, San Diego, California) Receiver operating characteristic curves (ROC) were generated using the R software environment for statistical computing and graphics (R Foundation for Statistical Computing, Vienna, Austria.)

Table 15 which follows provides an ROC analysis and diagnostic performance for various salivary biomarker combinations, namely, NSE (A), GFAP (B), UCH-L1 (C), IL-1β (D), IFN-γ (E), IL-8(F), IL-10 (G), Spectrin II (H) and 8-OHdG (I) for the diagnosis of and discrimination between subjects with mTBI and control subjects.

TABLE 15

ROC Analysis and Diagnostic Performance for Various Biomarker Combinations

| | A | AB | ABC | ABCD | ABCDE | ABCD-EF | ABCD-EFG | ABCD-EFGH | ABCD-EFGHI |
|---|---|---|---|---|---|---|---|---|---|
| AUC | 0.95 | 0.95 | 0.95 | 0.95 | 0.95 | 0.95 | 0.95 | 0.95 | 0.95 |
| Sensitivity | 0.85 | 0.86 | 0.89 | 0.90 | 0.90 | 0.93 | 0.95 | 0.95 | 0.98 |
| Specificity | 0.85 | 0.85 | 0.88 | 0.89 | 0.92 | 0.94 | 0.94 | 0.95 | 0.97 |

The ROC analysis established diagnostic sensitivity and specificity for mTBI as shown in Table 15. The combination models NSE (A), GFAP (B), UCH-L1 (C), IL-1β (D), IFN-γ (E), IL-8(F), IL-10 (G), Spectrin II (H) and 8-OHdG (I) have high diagnostic values for diagnosis of mTBI as compared to other combination models i.e. individual biomarker only. Accordingly, it can be expected that the combination of any two or more of the biomarkers in Table 15 would have high diagnostic values for screening, monitoring, diagnosis, and prognosis of mTBI. The efficacy of biomarker pairs selected from Table 15 in detecting mTBI is further confirmed by the data of Example 2, Tables 3-6 where IL-8 and UCH-L1, UCH-L1 and NSE, and UCH-L1 and GFAP were respectively demonstrated to be effective in detecting mTBI in adolescent children young adult, and older populations. It is expected that the foregoing biomarkers would be effective in identifying mTBI in adolescent children as young as age six (6) through adults as old as age ninety (90), and even older.

Example 4

Example 4 was conducted to evaluate the reproducibility and stability of salivary biomarkers. According to Example 4, saliva samples from twenty (20) athletes with sport-related concussion (SRC) and twenty (20) athlete control subjects (AC) were taken from the subjects of Example 1 above. The samples were randomly arranged and labeled such that the laboratory could not identify the individuals sampled.

For each analysis, the assay reproducibility of blinded quality control replicates was examined using the coefficient of variation (CV), a commonly used statistical analysis technique to describe laboratory technical error, and a determination was made of the effect of delayed sample processing on analyte concentrations in frozen samples at −80° C. (at twenty four hours, seven days and fourteen days after sampling, i.e. reproducibility with delayed processing.) Reproducibility was assessed over a one-week and two-week period for salivary biomarkers, by taking samples at seven days and fourteen days. The CV was determined by estimating the SD (standard deviation) of the quality control values, divided by the mean of these values, multiplied by 100. Inter-observer and intra-observer variances were estimated from repeated sample measurements using a random effects model, with sample identification number as the random variable.

To assess reproducibility, the ICC (Intraclass Correlation Coefficient) values were calculated by dividing the intra-observer variance by the sum of the within- and inter-observer variances. Ninety-five percent (95%) confidence intervals (CI) were also calculated. The inter- and intra-observer CVs were determined by taking the square root of the inter- and intra-observer variance components from the random effects mixed model on the In [log] transformed scale, with approximate estimates derived by the eta method. (Rosner B, Fundamentals of Biostatistics. Belmont, Calif.: Duxbury; 2006.) An ICC of <0.40 indicates poor reproducibility, an ICC of 0.40 to 0.8 indicates fair to good reproducibility, and an ICC of more than 0.8 indicates excellent reproducibility. Results are shown in Tables 16 and 17. Table 16 provides ICCs calculated for delayed analysis and processing of a single frozen sample at day one, day seven, and day fourteen for salivary biomarkers in subjects. Tables 16-17 provide ICCs calculated of samples tested at various time points (day one, day 20 seven and day fourteen) in all subjects.

TABLE 16

Intraclass Correlation Coefficient - Single Saliva Sample in Subjects

| Bio-marker | Number of participants/number of time points | Intra-observer CV (%) | | | Inter-observer CV (%) | | | ICC (95% CIs) | | |
|---|---|---|---|---|---|---|---|---|---|---|
| | | Day 1 | Day 7 | Day 14 | Day 1 | Day 7 | Day 14 | Day 1 | Day 7 | Day 14 |
| NSE | 40/3 | 1.2 | 1.3 | 1.2 | 2.2 | 2.3 | 2.4 | 0.92 | 0.92 | 0.92 |
| GFAP | 40/3 | 1.3 | 1.4 | 1.5 | 2.5 | 3.4 | 3.2 | 0.91 | 0.91 | 0.90 |
| UCH-L1 | 40/3 | 1.4 | 1.4 | 1.2 | 3.1 | 3.0 | 3.2 | 0.92 | 0.92 | 0.90 |
| IL-1β | 40/3 | 1.3 | 1.4 | 1.6 | 2.8 | 2.9 | 3.0 | 0.94 | 0.92 | 0.91 |
| IFN-γ | 40/3 | 1.4 | 1.5 | 1.6 | 2.7 | 2.5 | 3.2 | 0.93 | 0.92 | 0.90 |
| IL-8 | 40/3 | 1.2 | 1.4 | 1.2 | 2.5 | 3.0 | 3.5 | 0.92 | 0.94 | 0.94 |
| IL-10 | 40/3 | 1.3 | 1.2 | 1.2 | 2.9 | 3.2 | 2.9 | 0.91 | 0.92 | 0.93 |
| Spectrin II | 40/3 | 1.1 | 1.5 | 1.5 | 2.2 | 2.4 | 3.1 | 0.92 | 0.93 | 0.90 |
| 8-OHdG | 40/3 | 1. | 1.3 | 1.4 | 2.4 | 2.0 | 3.1 | 0.91 | 0.92 | 0.91 |

TABLE 17

Intraclass Correlation Coefficient - Time Point Testing in All Subjects

| Biomarker | Number of participants/ number of time points | Intra-ob server CV (%) | | | Inter-observer CV (%) | | | ICC (95% CIs) | | |
|---|---|---|---|---|---|---|---|---|---|---|
| | | Day 1 | Day 7 | Day 14 | Day 1 | Day 7 | Day 14 | Day 1 | Day 7 | Day 14 |
| NSE | 40/3 | 1.2 | 1.3 | 1.3 | 2.7 | 2.9 | 3.2 | 0.91 | 0.92 | 0.90 |
| GFAP | 40/3 | 1.1 | 1.2 | 2.0 | 2.4 | 2.8 | 3.5 | 0.91 | 0.92 | 0.91 |
| UCH-L1 | 40/3 | 1.3 | 1.6 | 1.7 | 2.5 | 2.9 | 3.5 | 0.93 | 0.95 | 0.98 |
| IL-1β | 40/3 | 1.5 | 1.5 | 1.7 | 2.6 | 3.2 | 3.6 | 0.89 | 0.88 | 0.89 |
| IFN-γ | 40/3 | 1.2 | 1.6 | 2.3 | 2.7 | 2.6 | 3.4 | 0.91 | 0.95 | 0.92 |
| IL-8 | 40/3 | 1.3 | 1.5 | 1.7 | 2.6 | 2.9 | 3.3 | 0.93 | 0.91 | 0.91 |
| IL-10 | 40/3 | 1.2 | 1.2 | 1.3 | 2.5 | 2.7 | 3.2 | 0.91 | 0.92 | 0.91 |
| Spectrin II | 40/3 | 1.3 | 1.6 | 1.7 | 2.4 | 3.2 | 3.1 | 0.91 | 0.91 | 0.88 |
| 8-OHdG | 40/3 | 1.4 | 1.6 | 1.4 | 2.3 | 3.1 | 3.3 | 0.93 | 0.91 | 0.91 |

The data of Example 4 demonstrate that the ICCs for the range of salivary biomarkers were high (ICCs of 0.9-0.95), indicating good to excellent reproducibility and stability. Example 4 demonstrates that the biomarkers of the study are stable and easy to reproduce Those skilled in the art will recognize that numerous modifications and changes may be made to the preferred embodiments without departing from the scope of the claimed invention. It will, of course, be understood that modifications of the invention, in its various aspects, will be apparent to those skilled in the art, some being apparent only after study, others being matters of routine mechanical, chemical, and electronic design. No single feature, function, or property of the preferred embodiments are essential. Other embodiments are possible, their specific designs depending upon the particular application. As such, the scope of the invention should not be limited by the particular embodiments herein described, but should be defined only by the appended claims and equivalents thereof

We claim:

1. A system for detecting traumatic brain injury (TBI) of at least mild severity (mTBI) in a human subject, comprising:

(a) at least one binding agent specific to a Ubiquitin Carboxy-Terminal Hydrolase L1 (UCH-L1) biomarker or UCH-L1 in combination with one or more biomarker selected from the group consisting of Neuron Specific Enolase (NSE), Glial Fibrillary Acidic Protein (GFAP), and Interleukin 8 (IL-8);

(b) a measurable label that indicates a proportional reaction based on the level of biomarker present in a saliva sample from the subject; and (c) a measurement device operable to provide a visible indication of the measurable label to provide a qualitative or quantitative level of one or more biomarkers in the saliva sample indicative that the subject has TBI, wherein the system detects when the one or more biomarkers are at the following concentrations in the saliva sample and such detection is indicative that the subject should be evaluated for possible TBI:

(i) NSE concentrations of between 0.8 pg/ml and 2.1 pg/ml;

(ii) GFAP concentrations of between 0.7 pg/ml and 2.5 pg/ml;

(iii) UCH-L1 concentrations of between 0.8 pg/ml and 65 pg/ml; and (iv) IL-8 concentrations of between 450 pg/ml and 950 pg/ml.

2. The system of claim 1, wherein the binding agent comprises an antibody binding agent.

3. The system of claim 2, further comprising at least one lateral flow substrate with the binding agent affixed thereto.

4. The system of claim 3, wherein the measurement device provides a visual indication of the measurable label.

5. The system of claim 4, wherein the visual indication is a fluorescent indication.

6. The system of claim 1, wherein the at least one binding agent is specific to the biomarkers IL-8 and UCH-L1.

7. The system of claim 1, wherein the at least one binding agent is specific to the biomarkers NSE and UCH-L1.

8. The system of claim 1, wherein the at least one binding agent is specific to the biomarkers GFAP and UCH-L1.

9. The system of claim 1, wherein a combination of any two of the biomarkers is effective at detecting TBI in adolescent, youth, and older populations aged six through at least ninety years.

10. The system of claim 1, wherein the system detects that the subject can return to play (RTP) within about twenty minutes to about two weeks following a suspected TBI.

11. The system of claim 10, wherein the system detects that the subject can return to play (RTP) within about four to eight hours following the suspected TBI.

12. The system of claim 11, wherein the system detects that the subject can return to play (RTP) within about six hours following the suspected TBI.

13. The system of claim 1, wherein the system is capable of differentiating differentiates TBI from injuries unrelated to TBI.

14. The system of claim 1, wherein the measurement device detects that the level of the one or more biomarkers in the saliva sample is at or above a reference level.

15. The system of claim 14, wherein the indication that the level of the one or more biomarkers in the saliva sample is at or above the reference level is indicative that the subject should not return to play (RTP).

16. The system of claim 1, wherein the system is an in vitro system.

17. The system of claim 1, wherein the system is a point-of-care test platform.

18. The system of claim 17, wherein the point-of-care test platform is a kit.

19. The system of claim 17, wherein the system includes a mouth guard appliance and the mouth guard appliance includes the at least one binding agent.

20. A system for detection of possible mild traumatic brain injury (mTBI) or more severe traumatic brain injury (TBI) in a human subject within 6 hours after a head injury event, the system comprising:

(a) at least one binding agent specific to a Ubiquitin Carboxy-Terminal Hydrolase L1 (UCH-L1) biomarker or UCH-L1 in combination with one or more biomarker, the one or more biomarker being selected from the group consisting of Neuron Specific Enolase (NSE), Glial Fibrillary Acidic Protein (GFAP), and Interleukin 8 (IL-8);

(b) a measurable label that indicates a proportional reaction based on the level of biomarker present in a saliva sample from the subject; and (c) a measurement device which provides a visible indication of the measurable label when the one or more biomarker in the subject's saliva sample is at or above the following concentrations:

(i) NSE at or above about 1 pg/ml;

(ii) GFAP at or above of about 1 pg/ml;

(iii) UCH-L1 at or above about 10 pg/ml; and (iv) IL-8 at or above about 400 pg/ml, whereby, appearance of the indication means that the subject should be evaluated for possible mTBI or TBI.

21. The system of claim 20 wherein the visible indication is provided when the one or more biomarker in the subject's saliva sample is at or above the following concentrations:

(i) NSE at or above about 1.5 pg/ml;

(ii) GFAP at or above of about 1.8 pg/ml;

(iii) UCH-L1 at or above about 13.6 pg/ml; and (iv) IL-8 at or above about 624 pg/ml.

22. The system of claim 21 wherein the visible indication is provided when the one or more biomarker in the subject's saliva sample is at or above the following concentrations within about 1 to about 6 hours after the head injury:

(i) NSE at or above about 1.8 pg/ml;

(ii) GFAP at or above of about 1.9 pg/ml;

(iii) UCH-L1 at or above about 54 pg/ml; and (iv) IL-8 at or above about 709 pg/ml.

23. The system of claim 20, wherein the binding agent comprises an antibody binding agent.

24. The system of claim 23, wherein the measurement device comprises a lateral flow substrate with the binding agent affixed thereto.

25. The system of claim 24, wherein a visual indication of the measurable label is provided on the lateral flow substrate when the one or more biomarker is captured by the binding agent and is present in an amount at or above the concentration.

26. The system of claim 25, wherein the visual indication is a fluorescent indication.

27. The system of claim 20, wherein the at least one binding agent is specific to the biomarkers IL-8 and UCH-L1.

28. The system of claim 27, wherein the system consisting of the at least one binding agent specific to the biomarkers IL-8 and UCH-L1 detects mTBI in a subject with a correlation of at least about 0.92 within one hour after the head injury event.

29. The system of claim 20, wherein the at least one binding agent is specific to the biomarkers NSE and UCH-L1.

30. The system of claim 29, wherein the system consisting of the at least one binding agent specific to the biomarkers NSE and UCH-L1 detects mTBI in a subject with a correlation of at least about 0.89 within one hour after the head injury event.

31. The system of claim 20, wherein the at least one binding agent is specific to the biomarkers GFAP and UCH-L1.

32. The system of claim 31, wherein the system consisting of the at least one binding agent specific to the biomarkers GFAP and UCH-L1 detects mTBI in a subject with a correlation of at least about 0.89 within one hour after the head injury event.

33. The system of claim 20, wherein a combination of any two of the biomarkers is effective at detecting TBI in adolescent, youth, and older populations aged six through at least ninety years.

34. The system of claim 20, wherein the system provides the indication within about twenty minutes to about two weeks following the head injury event and the indication means that the subject should not return to play (RTP).

35. The system of claim 20, wherein the system provides the indication within about one hour following the head injury event and the indication means that the subject should not return to play (RTP).

* * * * *